US012577307B2

(12) United States Patent
Ishikura et al.

(10) Patent No.: US 12,577,307 B2
(45) Date of Patent: Mar. 17, 2026

(54) METHOD AND MEDICAMENT FOR TREATING CANCER UNRESPONSIVE TO PD-1/PD-L1 SIGNALING INHIBITOR

(71) Applicant: Genentech, Inc., South San Francisco, CA (US)

(72) Inventors: Nobuyuki Ishikura, Kanagawa (JP); Toshiki Iwai, Kanagawa (JP); Masamichi Sugimoto, Kanagawa (JP)

(73) Assignee: Genentech, Inc., South San Francisco, CA (US)

( * ) Notice: Subject to any disclaimer, the term of this patent is extended or adjusted under 35 U.S.C. 154(b) by 1235 days.

(21) Appl. No.: 17/290,197

(22) PCT Filed: Oct. 17, 2019

(86) PCT No.: PCT/IB2019/058848
§ 371 (c)(1),
(2) Date: Apr. 29, 2021

(87) PCT Pub. No.: WO2020/089722
PCT Pub. Date: May 7, 2020

(65) Prior Publication Data
US 2021/0388090 A1     Dec. 16, 2021

(30) Foreign Application Priority Data

Oct. 31, 2018     (JP) ................................. 2018-206076

(51) Int. Cl.
| C07K 16/28 | (2006.01) |
| A61K 39/00 | (2006.01) |
| A61P 35/00 | (2006.01) |
| C07K 16/22 | (2006.01) |

(52) U.S. Cl.
CPC .......... C07K 16/2827 (2013.01); A61P 35/00 (2018.01); C07K 16/22 (2013.01); C07K 16/2818 (2013.01); A61K 39/00 (2013.01); A61K 2039/507 (2013.01)

(58) Field of Classification Search
None
See application file for complete search history.

(56) References Cited

U.S. PATENT DOCUMENTS

| 8,217,149 | B2 | 7/2012 | Irving |
| 9,920,123 | B2 | 3/2018 | Irving |
| 2010/0203056 | A1 | 8/2010 | Irving |
| 2013/0045200 | A1 | 2/2013 | Irving |
| 2013/0045201 | A1 | 2/2013 | Irving |
| 2013/0045202 | A1 | 2/2013 | Irving |
| 2014/0065135 | A1 | 3/2014 | Irving |
| 2015/0322153 | A1 | 11/2015 | Irving |
| 2016/0222117 | A1 | 8/2016 | Irving |
| 2017/0107287 | A1 | 4/2017 | Irving |
| 2019/0016807 | A1 | 1/2019 | Irving |
| 2021/0032345 | A1 | 2/2021 | Irving et al. |

FOREIGN PATENT DOCUMENTS

| JP | 2012511329 | A | 5/2012 |
| JP | 2017506227 | A | 3/2017 |
| JP | 2018522850 | A | 8/2018 |
| JP | 2018522887 | A | 8/2018 |
| JP | 2018529375 | A | 10/2018 |
| WO | 2010077634 | A1 | 7/2010 |
| WO | 2015095418 | A1 | 6/2015 |
| WO | 2015119930 | A1 | 8/2015 |
| WO | 2016205277 | A1 | 12/2016 |
| WO | 2017011666 | A1 | 1/2017 |
| WO | 2017020802 | A1 | 2/2017 |
| WO | 2018160841 | A1 | 9/2018 |

OTHER PUBLICATIONS

Sznol et al., Phase Ib evaluation of MPDL3280A (anti-PDL1) in combination with bevacizumab (bev) in patients (pts) with metastatic renal cell carcinoma (mRCC). Journal of Clinical Oncology, vol. 33, No. 7, suppl. 410, Mar. 1, 2015.*

Bendell et al., Safety and efficacy of MPDL3280A (anti-PDL1) in combination with bevacizumab (bev) and/or Folfox in patients (pts) with metastatic colorectal cancer (mCRC). Journal of Clinical Oncology, vol. 33, No. 3, suppl. 704, Jan. 20, 2015.* 2015.*

Chen, D.S. et al. (Jul./Aug. 2018). "Combinations of Bevacizumab With Cancer Immunotherapy," Cancer J. 24(4):193-204.

International Preliminary Report on Patentability, issued Apr. 27, 2021, for PCT Application No. PCT/IB2019/058848, filed Oct. 17, 2019, 6 pages.

International Search Report and Written Opinion, mailed Nov. 26, 2019, for PCT Application No. PCT/IB2019/058848, filed Oct. 17, 2019, 10 pages.

Meder, L. et al. (May 18, 2018). "Combined VEGF and PD-L1 Blockade Displays Synergistic Treatment Effects in an Autochthonous Mouse Model of Small Cell Lung Cancer," Cancer Research 78(15):4270-4281.

U.S. Appl. No. 17/108,983, Irving et al., filed Dec. 1, 2020.(Copy not submitted herewith pursuant to the waiver of 37 C.F.R. § 1.98(a)(2)(iii) issued by the Office on Sep. 21, 2004).

U.S. Appl. No. 17/398,842, Irving et al., filed Aug. 10, 2021.(Copy not submitted herewith pursuant to the waiver of 37 C.F.R. § 1.98(a)(2)(iii) issued by the Office on Sep. 21, 2004).

Weber, W.A. (2009). "Assessing Tumor Response to Therapy," J. Nucl. Med. 50:1S-10S.

WHO Drug Information (2014). "International Nonproprietary Names From Pharmaceutical Substances (INN)," INN 28(4):485-563.

Constantinidou, A. et al. (Feb. 2019, e-pub. Sep. 28, 2018). "Targeting Programmed Cell Death-1 (PD-1) and Ligand (PD-L1): A New Era In Cancer Active Immunotherapy," Pharmacology & Therapeutics, 194:84-106.

(Continued)

*Primary Examiner* — Ruixiang Li
(74) *Attorney, Agent, or Firm* — Morrison & Foerster LLP

(57)     ABSTRACT

The present invention relates to medicaments, treatment methods, kits, and uses for treating cancer in individuals, characterized in that a VEGF signaling inhibitor and a PD-1/PD-L1 signaling inhibitor are administered in combination, as well as VEGF signaling inhibitors, PD-1/PD-L1 signaling inhibitors, and combinations thereof.

8 Claims, 7 Drawing Sheets

Specification includes a Sequence Listing.

(56) References Cited

OTHER PUBLICATIONS

Extended European Search Report, dated Aug. 5, 2022, for European Patent Application No. 19880708.03, 13 pages.
Gao, X, et al. (Jul./Aug. 1, 2018). "Combinations of Bevacizumab With Immune Checkpoint Inhibitors in Renal Cell Carcinoma," Cancer Journal 24(4):171-179.
McDermott, D. et al. (Jun. 4, 2018). "Clinical Activity and Molecular Correlates of Response to Atezolizumab Alone or in Combination With Bevacizumab Versus Sunitinib in Renal Cell Carcinoma," Nature Medicine 24(6):749-757, 27 pages.

O'Donnell, U.S et al. (Jan. 2017, e-pub. Nov. 27, 2016). "Resistance to PD1/PDL1 Checkpoint Inhibition," Cancer Treatment Reviews 52:71-81.
Socinski, M.A. et al. (Jun. 14, 2018). "Atezolizumab for First-Line Treatment of Metastatic Nonsquamous NSCLC," New England Journal of Medicine 378(24):2288-2301.
Zhang, L. et al. (Apr. 26, 2019). "Atezolizumab and Bevacizumab Attenuate Cisplatin Resistant Ovarian Cancer Cells Progression Synergistically via Suppressing Epithelial-Mesenchymal Transition," Frontiers in Immunology 10:867, 14 pages.
Gaillard, S.L. et al. (2016). "The Role of Immune Checkpoint Inhibition in the Treatment of Ovarian Cancer," Gynecologic Oncology Research and Practice 3:11, 14 pages.

* cited by examiner

[Fig. 1]
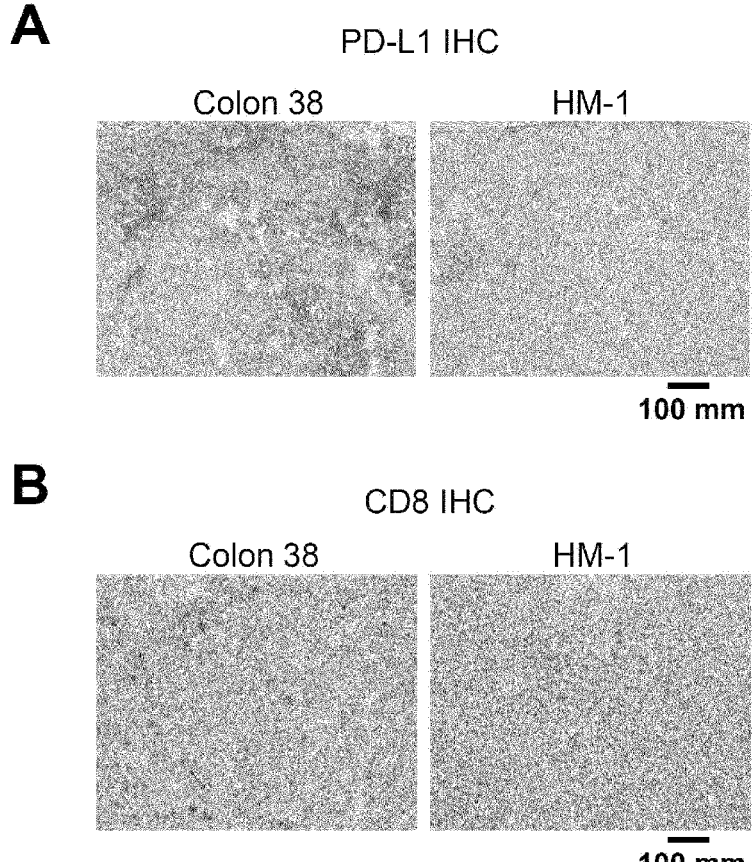
A     PD-L1 IHC
Colon 38     HM-1
100 mm
B     CD8 IHC
Colon 38     HM-1
100 mm

[Fig. 2]
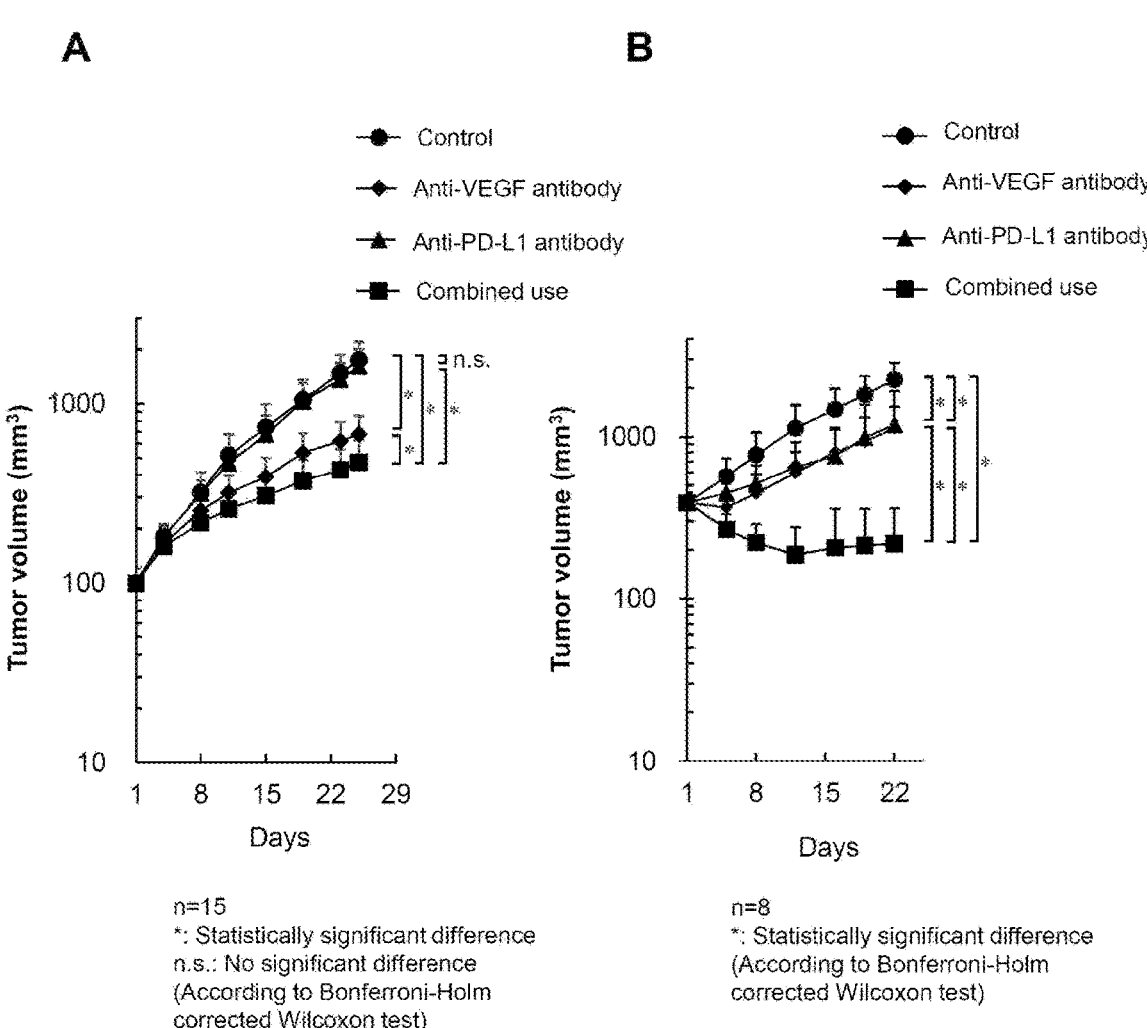

[Fig. 3]

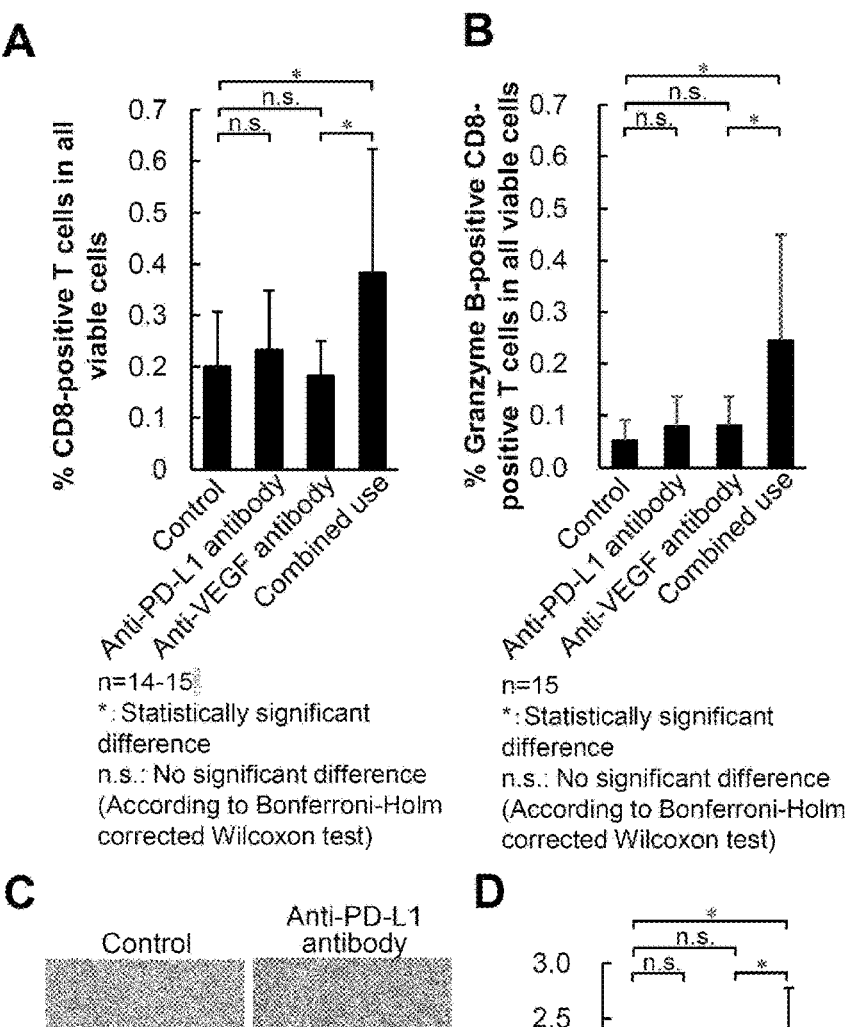

A n=14-15
* : Statistically significant
difference
n.s.: No significant difference
(According to Bonferroni-Holm
corrected Wilcoxon test)

B n=15
* : Statistically significant
difference
n.s.: No significant difference
(According to Bonferroni-Holm
corrected Wilcoxon test)

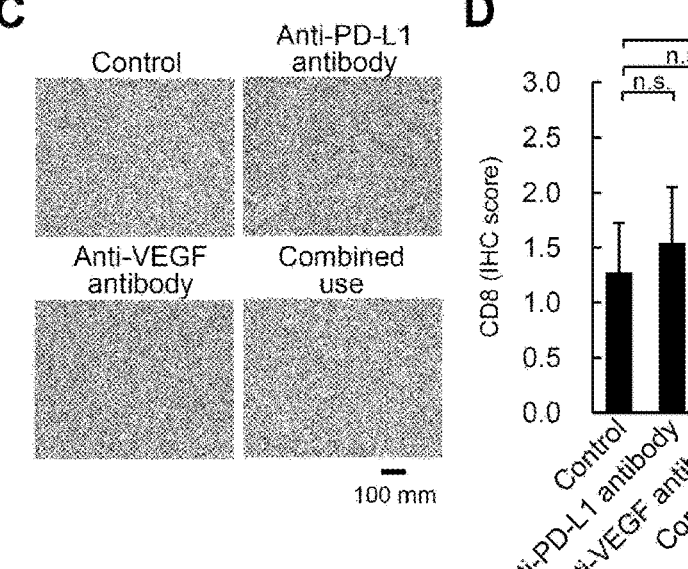

C

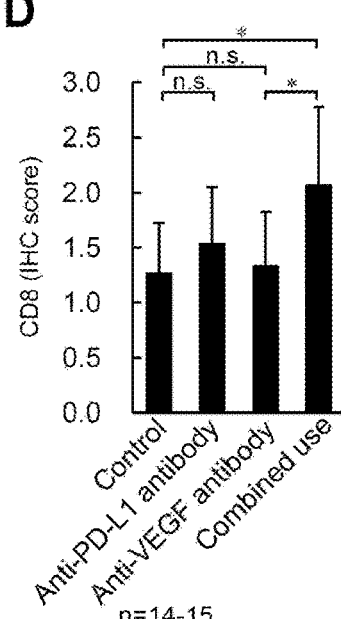

D n=14-15
* : Statistically significant difference
n.s.: No significant difference
(According to Bonferroni-Holm
corrected Wilcoxon test)

[Fig. 4]
A
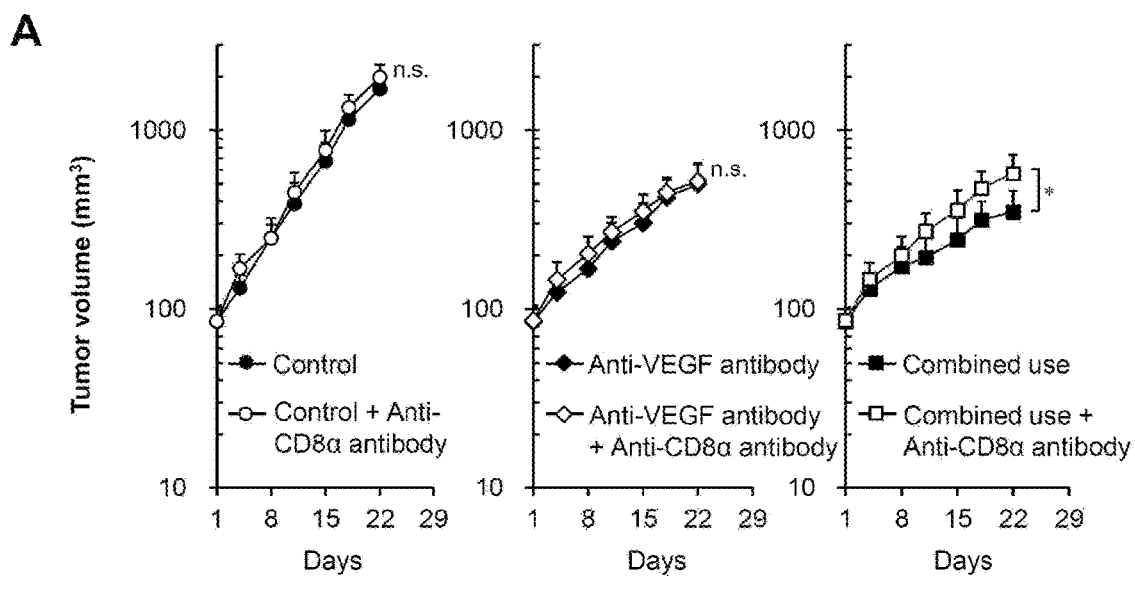
n=14
*: Statistically significant difference
n.s.: No significant difference
(According to Bonferroni-Holm
 corrected Wilcoxon test)
B
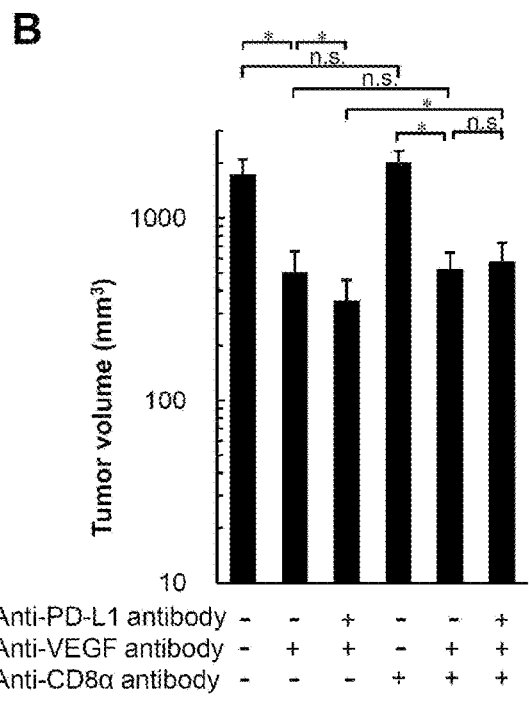
| Anti-PD-L1 antibody | − | − | + | − | − | + |
| Anti-VEGF antibody | − | + | + | − | + | + |
| Anti-CD8α antibody | − | − | − | + | + | + |
n=14
*: Statistically significant
difference
n.s.: No significant difference
(According to Bonferroni-
Holm corrected Wilcoxon test)

[Fig. 5]
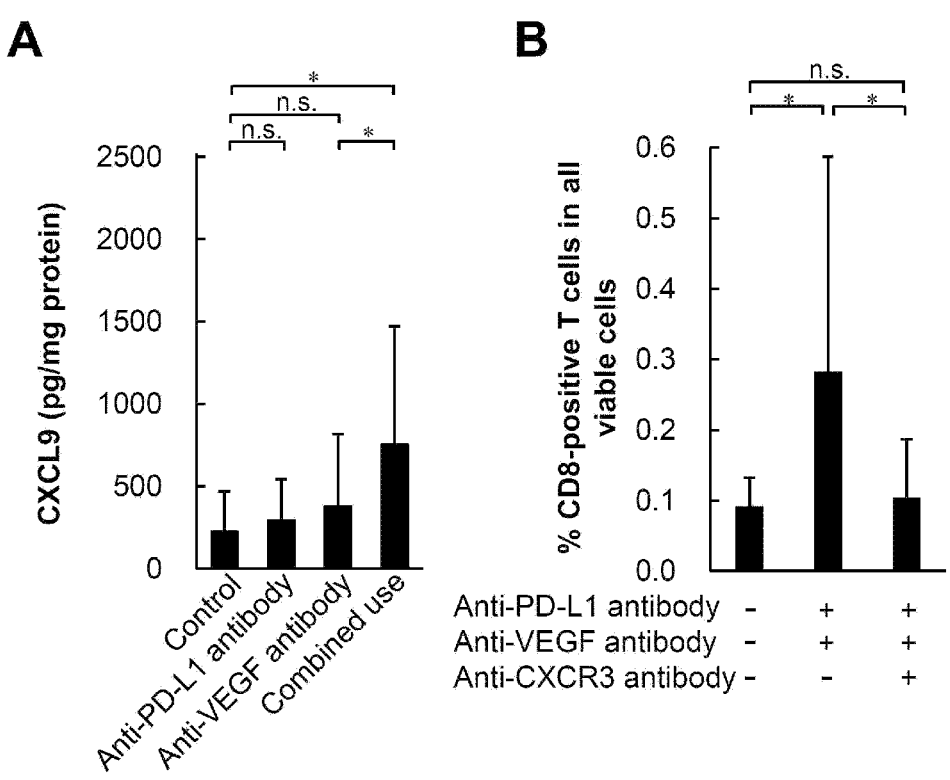
n=14-15/group
*: Statistically significant
difference
n.s.: No significant difference
(According to Bonferroni-Holm
corrected Wilcoxon test)
n=16/group
*: Statistically significant
difference
n.s.: No significant difference
(According to Bonferroni-Holm
corrected Wilcoxon test)

[Fig. 6]
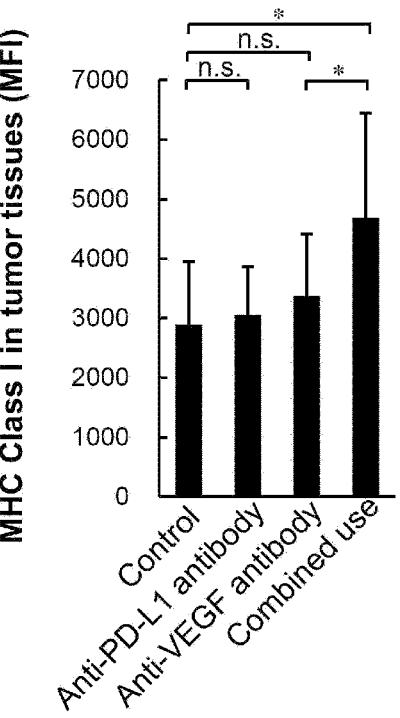
n=15
* : Statistically significant difference
n.s.: No significant difference
(According to Bonferroni-Holm corrected Wilcoxon test)

[Fig. 7]
A
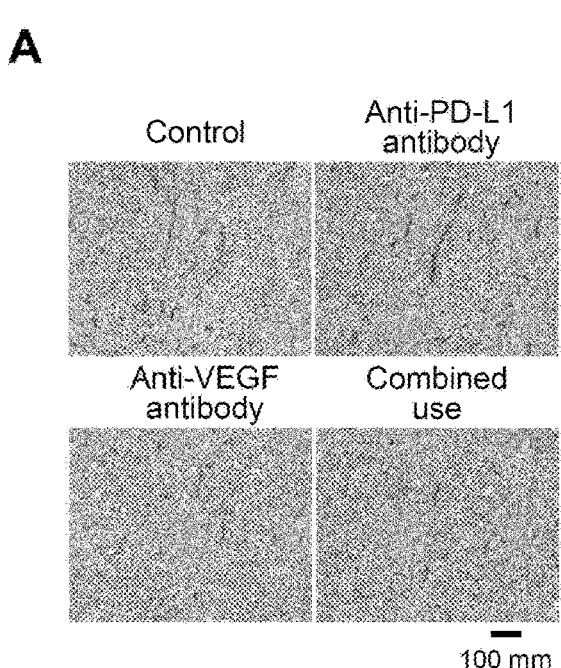
Control     Anti-PD-L1 antibody
Anti-VEGF antibody     Combined use
100 mm
B
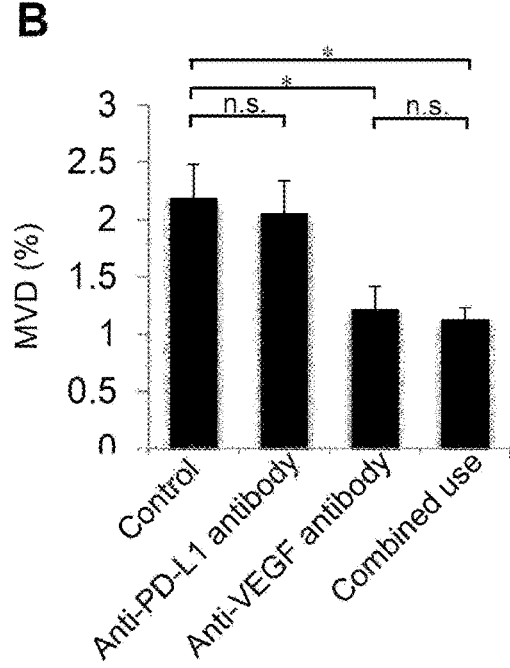
n=7
*: Statistically significant difference
n.s.: No significant difference
(According to Bonferroni-Holm corrected Wilcoxon test)

METHOD AND MEDICAMENT FOR TREATING CANCER UNRESPONSIVE TO PD-1/PD-L1 SIGNALING INHIBITOR

CROSS REFERENCE TO RELATED APPLICATIONS

This application is a national stage application under 35 U.S.C. § 371 of International Application No. PCT/IB2019/058848, filed internationally on Oct. 17, 2019, which claims priority of International Application JP 2018-206076, filed Oct. 31, 2018, which are incorporated herein by reference in their entirety.

TECHNICAL FIELD

The present invention relates to medicaments, treatment methods, kits, and uses as well as VEGF signaling inhibitors, PD-1/PD-L1 signaling inhibitors, and combinations thereof for treating cancer in individuals, characterized in that a VEGF signaling inhibitor and a PD-1/PD-L1 signaling inhibitor are administered in combination. More specifically, the present invention relates to medicaments, treatment methods, kits, and uses as well as VEGF signaling inhibitors, PD-1/PD-L1 signaling inhibitors, and combinations thereof for treating cancer unresponsive to a PD-1/PD-L1 signaling inhibitor in individuals, characterized in that a VEGF signaling inhibitor and a PD-1/PD-L1 signaling inhibitor are administered in combination.

BACKGROUND ART

Programmed cell death 1 (PD-1) receptor and PD-1 ligands 1 and 2 (respectively PD-L1 and PD-L2) play important roles in immunomodulation. PD-1, which is expressed on activated T cells, is activated by PD-L1 (also known as B7-H1) and PD-L2, which are expressed by stromal cells, tumor cells, or both, and amplification of PD-1 signaling causes T cells to lose the ability to replicate and the ability to attack cancer cells, ultimately leading to cell death. Administration of signaling inhibitors of these proteins, e.g., anti-PD-1 antibodies or anti-PD-L1 antibodies, re-activates T cells and restores cytotoxic immune functions.

Human vascular endothelial growth factor (VEGF/VEGF-A) is involved in the restriction of normal and abnormal angiogenesis and neovascularization associated with tumors and intraocular disorders. VEGF is a homodimeric glycoprotein isolated from multiple sources. For endothelial cells, VEGF exhibits an activity that promotes the division thereof. VEGF has important regulatory functions in the formation of new vessels during fetal vasculogenesis and in angiogenesis in adulthood. As of October 2018, three products have received approvals for manufacture and sales in Japan as agents called angiogenic inhibitors (VEGF inhibitors). The three products are bevacizumab (proprietary name: Avastin), ramucirumab (proprietary name: Cyramza), and aflibercept (proprietary name: Zaltrap).

Nivolumab (proprietary name: Opdivo) and pembrolizumab (proprietary name: Keytruda) are commercially available anti-PD-1 antibodies, and atezolizumab (proprietary name: Tecentriq) and avelumab (proprietary name: Bavencio), and durvalumab (proprietary name: Imfinzi) are commercially available anti-PD-L1 antibodies.

As of October 2018, ipilimumab (proprietary name: Yervoy), an anti-CTLA4 antibody, is the only agent approved for combined use with these PD-1/PD-L1 signaling inhibitors. PD-1/PD-L1 signaling inhibitors are otherwise administered as single agents.

However, more effective therapies, with the synergistic effects of using an anti-cancer agent and immunotherapy in combination, are still being sought (Non-Patent Reference 1). Combinations of PD-1/PD-L1 signaling inhibitors and VEGF signaling inhibitors are also being developed (Patent References 1-5).

PATENT LITERATURE

Patent Literature 1 JP 2012-511329 A
Patent Literature 2 JP 2017-506227 A
Patent Literature 3 JP 2018-522887 A
Patent Literature 4 JP 2018-529375 A
Patent Literature 5 JP 2018-522850 A

Non Patent Literature

Non Patent Literature 1 Cancer J. 2018 July/August; 24(4): 193-204.

SUMMARY OF INVENTION

The present invention provides medicaments, treatment methods, kits, and uses as well as VEGF signaling inhibitors, PD-1/PD-L1 signaling inhibitors, and combinations thereof for treating cancer. More specifically, the present invention provides medicaments, treatment methods, kits, uses as well as VEGF signaling inhibitors, PD-1/PD-L1 signaling inhibitors, and combinations thereof for treating cancer unresponsive to a PD-1/PD-L1 signaling inhibitor in individuals.

The present inventors discovered, with diligent studies, that the combination of a VEGF signaling inhibitor and a PD-1/PD-L1 signaling inhibitor is more effective, i.e., provides a synergistic effect, in cancer treatment than when the VEGF signaling inhibitor or PD-1/PD-L1 signaling inhibitor is each used separately. In particular, the present inventors discovered that the combination of a VEGF signaling inhibitor and a PD-1/PD-L1 signaling inhibitor is effective in the treatment of cancer unresponsive to a PD-1/PD-L1 signaling inhibitor, leading to the completion of the present invention.

The medicament according to the present invention is a medicament for treating cancer in an individual, comprising a PD-1/PD-L1 signaling inhibitor, for use in combination with a VEGF signaling inhibitor.

The medicament according to the present invention is a medicament for treating cancer in an individual, comprising a VEGF signaling inhibitor, for use in combination with a PD-1/PD-L1 signaling inhibitor.

The medicament according to the present invention is a medicament for treating cancer in an individual, comprising a VEGF signaling inhibitor and a PD-1/PD-L1 signaling inhibitor.

The medicament according to the present invention is a medicament for treating cancer in an individual, wherein a PD-1/PD-L1 signaling inhibitor and a VEGF signaling inhibitor are administered in combination.

Any one of the above medicaments according to the present invention is a medicament wherein the PD-1/PD-L1 signaling inhibitor and the VEGF signaling inhibitor are administered concurrently, separately, or sequentially.

Any one of the above medicaments according to the present invention is a medicament wherein the VEGF signaling inhibitor is a VEGF antagonist or a VEGFR antagonist.

Any one of the above medicaments according to the present invention is a medicament wherein the VEGF signaling inhibitor is an anti-VEGF antibody or an anti-VEGFR antibody.

Any one of the above medicaments according to the present invention is a medicament wherein the anti-VEGF antibody or the anti-VEGFR antibody is bevacizumab, ramucirumab, or aflibercept beta.

Any one of the above medicaments according to the present invention is a medicament wherein the PD-1/PD-L1 signaling inhibitor is a PD-1 antagonist or a PD-L1 antagonist.

Any one of the above medicaments according to the present invention is a medicament wherein the PD-1/PD-L1 signaling inhibitor is AMP-224, BMS-936559, MEDI4736, MSB0010718C, MPDL3280A, nivolumab, AMP-514, pembrolizumab (MK-3475), REGN2810, PDR001, BGB-A317, or pidilizumab (CT-011).

Any one of the above medicaments according to the present invention is a medicament wherein the PD-1/PD-L1 signaling inhibitor is an anti-PD-L1 antibody.

Any one of the above medicaments according to the present invention may be a medicament wherein the cancer is selected from a group consisting of breast cancer, liver cancer, lung cancer including small cell lung cancer, ovarian cancer, gastric cancer, bladder cancer, pancreatic cancer, biliary tract cancer, cervical cancer, endometrial cancer, colon cancer, rectal cancer, colorectal cancer, renal cancer, esophageal cancer, prostate cancer, malignant melanoma, head and neck cancer, malignant pleural mesothelioma, glioblastoma, urothelial cancer, soft tissue sarcoma, malignant lymphoma, multiple myeloma, virus-positive solid cancer, virus-negative solid cancer, leukemia, squamous cell carcinoma, Merkel cell carcinoma, pediatric malignant solid tumors, glioma, thyroid cancer, non-small cell lung cancer, Hodgkin's lymphoma, and uterine cancer.

The medicament according to the present invention is a medicament for treating cancer, comprising a PD-1/PD-L1 signaling inhibitor, for use in combination with a VEGF signaling inhibitor, wherein the medicament improves the response rate in a group comprising individuals who are in need of cancer treatment and are administered with the PD-1/PD-L1 signaling inhibitor and the VEGF signaling inhibitor concurrently, separately, or sequentially, as compared with when the PD-1/PD-L1 signaling inhibitor is administered not in combination with the VEGF signaling inhibitor.

The medicament according to the present invention is a medicament for treating cancer, comprising a VEGF signaling inhibitor, for use in combination with a PD-1/PD-L1 signaling inhibitor, wherein the medicament improves the response rate in a group comprising individuals who are in need of cancer treatment and are administered with the PD-1/PD-L1 signaling inhibitor and the VEGF signaling inhibitor concurrently, separately, or sequentially, as compared with when the VEGF signaling inhibitor is administered not in combination with the PD-1/PD-L1 signaling inhibitor.

The medicament according to the present invention is a medicament for treating cancer, comprising a PD-1/PD-L1 signaling inhibitor and a VEGF signaling inhibitor, wherein the medicament improves the response rate in a group comprising individuals who are in need of cancer treatment and are administered with the PD-1/PD-L1 signaling inhibitor and the VEGF signaling inhibitor concurrently, separately, or sequentially, as compared with when the PD-1/PD-L1 signaling inhibitor is administered not in combination with the VEGF signaling inhibitor or when the VEGF signaling inhibitor is administered not in combination with the PD-1/PD-L1 signaling inhibitor.

The kit according to the present invention is a kit for treating cancer in an individual, comprising a PD-1/PD-L1 signaling inhibitor, for use in combination with a VEGF signaling inhibitor.

The kit according to the present invention is a kit for treating cancer in an individual, comprising a VEGF signaling inhibitor, for use in combination with a PD-1/PD-L1 signaling inhibitor.

The kit according to the present invention is a kit for treating cancer in an individual, comprising a VEGF signaling inhibitor and a PD-1/PD-L1 signaling inhibitor.

The kit according to the present invention is a kit for treating cancer, wherein a PD-1/PD-L1 signaling inhibitor and a VEGF signaling inhibitor are administered in combination.

Any one of the above kits according to the present invention is a kit wherein the PD-1/PD-L1 signaling inhibitor and the VEGF signaling inhibitor are administered concurrently, separately, or sequentially.

Any one of the above kits according to the present invention is a kit wherein the VEGF signaling inhibitor is a VEGF antagonist or a VEGFR antagonist.

Any one of the above kits according to the present invention is a kit wherein the VEGF signaling inhibitor is an anti-VEGF antibody or an anti-VEGFR antibody.

Any one of the above kits according to the present invention is a kit wherein the anti-VEGF antibody or the anti-VEGFR antibody is bevacizumab, ramucirumab, or aflibercept beta.

Any one of the above kits according to the present invention is a kit wherein the PD-1/PD-L1 signaling inhibitor is a PD-1 antagonist or a PD-L1 antagonist.

Any one of the above kits according to the present invention is a kit wherein the PD-1/PD-L1 signaling inhibitor is AMP-224, BMS-936559, MEDI4736, MSB0010718C, MPDL3280A, nivolumab, AMP-514, pembrolizumab (MK-3475), REGN2810, PDR001, BGB-A317, or pidilizumab (CT-011).

Any one of the above kits according to the present invention is a kit wherein the PD-1/PD-L1 signaling inhibitor is an anti-PD-L1 antibody.

Any one of the above kits according to the present invention may be a kit wherein the cancer is selected from a group consisting of breast cancer, liver cancer, lung cancer including small cell lung cancer, ovarian cancer, gastric cancer, bladder cancer, pancreatic cancer, biliary tract cancer, cervical cancer, endometrial cancer, colon cancer, rectal cancer, colorectal cancer, renal cancer, esophageal cancer, prostate cancer, malignant melanoma, head and neck cancer, malignant pleural mesothelioma, glioblastoma, urothelial cancer, soft tissue sarcoma, malignant lymphoma, multiple myeloma, virus-positive solid cancer, virus-negative solid cancer, leukemia, squamous cell carcinoma, Merkel cell carcinoma, pediatric malignant solid tumors, glioma, thyroid cancer, non-small cell lung cancer, Hodgkin's lymphoma, and uterine cancer.

The kit according to the present invention is a kit for treating cancer, comprising a PD-1/PD-L1 signaling inhibitor, for use in combination with a VEGF signaling inhibitor, wherein the kit improves the response rate in a group comprising individuals who are in need of cancer treatment and are administered with the PD-1/PD-L1 signaling inhibitor and the VEGF signaling inhibitor concurrently, separately, or sequentially, as compared with when the PD-1/

PD-L1 signaling inhibitor is administered not in combination with the VEGF signaling inhibitor.

The kit according to the present invention is a kit for treating cancer, comprising a VEGF signaling inhibitor, for use in combination with a PD-1/PD-L1 signaling inhibitor, wherein the kit improves the response rate in a group comprising individuals who are in need of cancer treatment and are administered with the PD-1/PD-L1 signaling inhibitor and the VEGF signaling inhibitor concurrently, separately, or sequentially, as compared with when the VEGF signaling inhibitor is administered not in combination with the PD-1/PD-L1 signaling inhibitor.

The kit according to the present invention is a kit for treating cancer, comprising a PD-1/PD-L1 signaling inhibitor and a VEGF signaling inhibitor, wherein the kit improves the response rate in a group comprising individuals who are in need of cancer treatment and are administered with the PD-1/PD-L1 signaling inhibitor and the VEGF signaling inhibitor concurrently, separately, or sequentially, as compared with when the PD-1/PD-L1 signaling inhibitor is administered not in combination with the VEGF signaling inhibitor or when the VEGF signaling inhibitor is administered not in combination with the PD-1/PD-L1 signaling inhibitor.

The treatment method according to the present invention is a method for treating cancer, comprising a step of administering, to an individual, one or more of the medicaments and kits and VEGF signaling inhibitors, PD-1/PD-L1 signaling inhibitors, and combinations thereof of the present invention in the respective embodiment described herein.

The use according to the present invention is a use of a PD-1/PD-L1 signaling inhibitor and/or a VEGF signaling inhibitor for the manufacture of a medicament or kit of the present invention.

The VEGF signaling inhibitor according to the present invention is a VEGF signaling inhibitor for use in cancer treatment and is administered in combination with a PD-1/PD-L1 signaling inhibitor to an individual in need thereof.

The PD-1/PD-L1 signaling inhibitor according to the present invention is a PD-1/PD-L1 signaling inhibitor for use in cancer treatment and is administered in combination with a VEGF signaling inhibitor to an individual in need thereof.

The combination according to the present invention is a combination of a VEGF signaling inhibitor and a PD-1/PD-L1 signaling inhibitor, for use in cancer treatment.

Advantageous Effects of Invention

The medicaments, treatment methods, kits, and uses as well as the VEGF signaling inhibitors, PD-1/PD-L1 signaling inhibitors, and combinations thereof according to the present invention can treat cancer in individuals more effectively than when a VEGF signaling inhibitor or a PD-1/PD-L1 signaling inhibitor is each used separately. More specifically, the present invention can treat cancer unresponsive to a PD-1/PD-L1 signaling inhibitor in an individual, more effectively than when a VEGF signaling inhibitor or a PD-1/PD-L1 signaling inhibitor is each used separately.

BRIEF DESCRIPTION OF DRAWINGS

FIG. 1 shows the baseline (unadministered) intratumoral expression of PD-L1 protein (A) and CD8 protein (B) in an OV2944-HM-1 cancer bearing mouse tumor tissue (HM-1) and in a Colon 38 cancer bearing mouse tumor tissue (Colon 38). For the OV2944-HM-1 cancer bearing mouse group, six were treated. For the Colon 38 cancer bearing mouse group, one (preliminary experiments performed on multiple individuals) was treated.

FIG. 2 shows changes in tumor volume of mouse ovarian cancer cell line OV2944-HM-1 (A) or mouse colorectal cancer cell line Colon 38 (B) in mice respectively administered with either a monotherapy (5 mg/kg of an anti-PD-L1 antibody (clone 6E11) twice a week or 10 mg/kg of an anti-VEGF antibody (clone B20-4.1.1) once a week), combined use of the anti-PD-L1 antibody and the anti-VEGF antibody, or a control antibody (control) at the same dosage. For each group, 15 (A) or eight (B) mice were treated. The average and SD bars of the tumor volume in each group were plotted.

FIG. 3 shows the proportion of CD8-positive T cells (A) and the proportion of granzyme B-positive CD8-positive T cells (B) in all viable cells in the tumors of OV2944-HM-1 cancer bearing mice on day 8 after initiation of administration in each administrated group set up similarly to that in FIG. 2A. For each group, 14-15 (A) and 15 (B) mice were treated. The average and SD bars of the cell proportion in each group were plotted. Additionally, the figure shows tissue sections (C), in which intratumoral CD8 protein was detected by immunohistochemistry in OV2944-HM-1 cancer bearing mice on day 8 after initiation of administration in each administered group set up similarly to that in FIG. 2A, and quantification of the expression thereof (D). For each group, 14-15 (C, D) mice were treated. The average and SD bars of the tumor volume in each group were plotted.

FIG. 4A shows changes over time in the tumor volume of OV2944-HM-1 cancer bearing mice in cases where an anti-CD8α antibody was used in combination (white (+anti-CD8α antibody)) and where the antibody was not used in combination (black) in the respective control group, anti-VEGF antibody single administration group, and anti-PD-L1 antibody and anti-VEGF antibody combined use group (combined use). For each group, 14 mice were treated. The average and SD bars of the tumor volume in each group were plotted. FIG. 4B shows the tumor volume of OV2944-HM-1 cancer bearing mice on day 22 after initiation of administration in each group administered (+) with the anti-PD-L1 antibody, the anti-VEGF antibody, the anti-CD8α antibody, or with the respective control antibody (−). For each group, 14 mice were treated. The average and SD bars of the tumor volume in each group were plotted.

FIG. 5A shows the expression of CXCL9 protein per 1 mg protein in the tumor tissues of OV2944-HM-1 cancer bearing mice on day 8 after initiation of administration in each administered group set up similarly to that in FIG. 2A. For each group, 14-15 mice were treated. The average and SD bars of the cell proportion in each group were plotted. FIG. 5B shows the proportion of CD8-positive T cells in all viable cells in the tumors of OV2944-HM-1 cancer bearing mice on day 8 after initiation of administration in each group administered (+) with the anti-PD-L1 antibody, the anti-VEGF antibody, and an anti-CXCR3 antibody, or with the respective control antibody (−). For each group, 16 mice were treated. The average and SD bars of the cell proportion in each group were plotted.

FIG. 6 shows the protein expression of MHC class I molecules, represented by mean fluorescence intensity (MFI), in the tumor tissues of OV2944-HM-1 cancer bearing mice on day 8 after initiation of administration in each administered group set up similarly to that in FIG. 2A. For each group, 15 mice were treated. The average and SD bars of the cell proportion in each group were plotted.

FIG. 7 shows tissue sections (A), in which intratumoral microvessel density (MVD) was detected by immunohisto-chemistry in the tumor tissues of OV2944-HM-1 cancer bearing mice on day 8 after initiation of administration in each administered group set up similarly to that in FIG. 2A, and quantification of MVD (B). For each group, seven mice were treated. The average and SD bars of the cell proportion in each group were plotted.

DESCRIPTION OF EMBODIMENTS

Embodiments of the present invention shall be explained in detail with examples below. Where there are no particular explanations in the embodiments and examples, the methods described in standard protocols, such as those in J. Sam-brook, E. F. Fritsch and T. Maniatis (Ed.), *Molecular cloning, a laboratory manual* (3rd edition), Cold Spring Harbor Press, Cold Spring Harbor, New York (2001) and F. M. Ausubel, R. Brent, R. E. Kingston, D. D. Moore, J. G. Seidman, J. A. Smith, K. Struhl (Ed.), *Current Protocols in Molecular Biology*, John Wiley & Sons Ltd., or modified and altered methods thereof are used. In addition, where commercially available reagent kits or measuring devices are used, the protocols attached thereto are used unless there are particular explanations.

Further, the objectives, characteristics, advantages, and ideas of the present invention are clear to those skilled in the art from the descriptions in the present specification, and based on the descriptions in the present specification, those skilled in the art would be able to easily reproduce the present invention. The embodiments and specific examples of the invention described below show preferred embodi-ments of the present invention. They are provided for the purpose of illustration or explanation and do not limit the present invention. It is clear to those skilled in the art that various alterations and modifications can be made based on the descriptions in the present specification within the aim and scope of the present invention disclosed herein.

==Medicaments According to the Present Invention==

The medicament according to the present invention is a medicament for treating cancer in an individual, wherein a PD-1/PD-L1 signaling inhibitor and a VEGF signaling inhibitor are administered in combination. In the medica-ment, the cancer is preferably a cancer resistant to a PD-1/PD-L1 signaling inhibitor.

The medicament according to the present invention is a medicament for treating cancer resistant to a PD-1/PD-L1 signaling inhibitor in an individual. The medicament, in one embodiment, comprises a PD-1/PD-L1 signaling inhibitor. The medicament is preferably a medicament for use in combination with a VEGF signaling inhibitor.

The medicament according to the present invention is a medicament for treating cancer resistant to a PD-1/PD-L1 signaling inhibitor in an individual. The medicament, in one embodiment, comprises a VEGF signaling inhibitor. The medicament is preferably a medicament for use in combi-nation with a PD-1/PD-L1 signaling inhibitor.

The medicament according to the present invention is a medicament for treating cancer in which resistance to a PD-1/PD-L1 signaling inhibitor has developed in an indi-vidual. The medicament, in one embodiment, comprises a VEGF signaling inhibitor and a PD-1/PD-L1 signaling inhibitor.

Any one of the above medicaments according to the present invention may be a medicament wherein the PD-1/PD-L1 signaling inhibitor and the VEGF signaling inhibitor are administered concurrently, separately, or sequentially. In addition, in any one of the above medicaments according to the present invention, the cancer may be a cancer which has intrinsic resistance or which has acquired resistance or has recurred.

The medicament according to the present invention is a medicament for treating cancer resistant to a PD-1/PD-L1 signaling inhibitor. The medicament, in one embodiment, comprises a PD-1/PD-L1 signaling inhibitor. The medica-ment is preferably a medicament for use in combination with a VEGF signaling inhibitor. In the medicament, the PD-1/PD-L1 signaling inhibitor and the VEGF signaling inhibitor may be administered concurrently, separately, or sequen-tially. The medicament, in one embodiment, improves the response rate in a group comprising individuals in need of treatment of cancer resistant to a PD-1/PD-L1 signaling inhibitor, as compared with when the PD-1/PD-L1 signaling inhibitor is administered not in combination with the VEGF signaling inhibitor.

The medicament according to the present invention is a medicament for treating cancer resistant to a PD-1/PD-L1 signaling inhibitor. The medicament, in one embodiment, comprises a VEGF signaling inhibitor. The medicament is preferably a medicament for use in combination with a PD-1/PD-L1 signaling inhibitor. In the medicament, the PD-1/PD-L1 signaling inhibitor and the VEGF signaling inhibitor may be administered concurrently, separately, or sequentially. The medicament, in one embodiment, improves the response rate in a group comprising individu-als in need of treatment of cancer resistant to a PD-1/PD-L1 signaling inhibitor, as compared with when the VEGF signaling inhibitor is administered not in combination with the PD-1/PD-L1 signaling inhibitor.

The medicament according to the present invention is a medicament for treating cancer resistant to a PD-1/PD-L1 signaling inhibitor. The medicament, in one embodiment, comprises a PD-1/PD-L1 signaling inhibitor and a VEGF signaling inhibitor. In the medicament, the PD-1/PD-L1 signaling inhibitor and the VEGF signaling inhibitor may be administered concurrently, separately, or sequentially. The medicament, in one embodiment, improves the response rate in a group comprising individuals in need of treatment of cancer resistant to a PD-1/PD-L1 signaling inhibitor, as compared with when the PD-1/PD-L1 signaling inhibitor is administered not in combination with the VEGF signaling inhibitor or when the VEGF signaling inhibitor is adminis-tered not in combination with the PD-1/PD-L1 signaling inhibitor.

With respect to the above medicaments according to the present invention, characterized by improvement of the response rate in the group comprising individuals in need of treatment of cancer resistant to a PD-1/PD-L1 signaling inhibitor, in one embodiment, the group comprising indi-viduals in need of treatment of cancer resistant to a PD-1/PD-L1 signaling inhibitor may include an individual not examined for the presence or absence of resistance through diagnosis prior to administration of the PD-1/PD-L1 signal-ing inhibitor. Alternatively, in another embodiment of the medicament, the group comprising individuals in need of treatment of cancer resistant to a PD-1/PD-L1 signaling inhibitor may include an individual who has been examined for the presence or absence of resistance and determined to be resistant through diagnosis prior to administration of the PD-1/PD-L1 signaling inhibitor. In yet another embodiment, the resistance may be resistance caused by conventional treatment comprising a PD-1/PD-L1 signaling inhibitor.

With respect to any one of the above medicaments according to the present invention, the VEGF signaling inhibitor may be a VEGF antagonist or a VEGFR antagonist.

With respect to any one of the above medicaments according to the present invention, the VEGF signaling inhibitor may be an anti-VEGF antibody or an anti-VEGFR antibody. In the medicament, the anti-VEGF antibody or the anti-VEGFR antibody is preferably bevacizumab, ramucirumab, or aflibercept beta.

With respect to any one of the above medicaments according to the present invention, the PD-1/PD-L1 signaling inhibitor may be a PD-1 antagonist or a PD-L1 antagonist. In the medicament, the PD-1 antagonist may be AMP-224, BMS-936559, MEDI4736, MSB0010718C, MPDL3280A, nivolumab, AMP-514, pembrolizumab (MK-3475), REGN2810, PDR001, BGB-A317, or pidilizumab (CT-011). In the medicament, the PD-1 antagonist is preferably an anti-PD-1 antibody, further preferably nivolumab, AMP-514, pembrolizumab (MK-3475), REGN2810, PDR001, BGB-A317, or pidilizumab (CT-011), and more preferably nivolumab or pembrolizumab. Moreover, in the medicament, the PD-L1 antagonist may be an anti-PD-L1 antibody. In the medicament, the PD-L1 antagonist may be durvalumab, atezolizumab, avelumab (MSB0010718C), BMS-936559, MPDL3280A, or MEDI4736 and is preferably durvalumab, atezolizumab, or avelumab.

Any one of the above medicaments according to the present invention may be a medicament wherein the cancer is selected from a group consisting of breast cancer, liver cancer, lung cancer including small cell lung cancer, ovarian cancer, gastric cancer, bladder cancer, pancreatic cancer, biliary tract cancer, cervical cancer, endometrial cancer, colon cancer, rectal cancer, colorectal cancer, renal cancer, esophageal cancer, prostate cancer, malignant melanoma, head and neck cancer, malignant pleural mesothelioma, glioblastoma, urothelial cancer, soft tissue sarcoma, malignant lymphoma, multiple myeloma, virus-positive solid cancer, virus-negative solid cancer, leukemia, squamous cell carcinoma, Merkel cell carcinoma, pediatric malignant solid tumors, glioma, thyroid cancer, non-small cell lung cancer, Hodgkin's lymphoma, and uterine cancer.

==Kits According to the Present Invention==

The kit according to the present invention is a kit comprising a VEGF signaling inhibitor and/or a PD-1/PD-L1 signaling inhibitor. In one embodiment, the kit is a kit for treating cancer in an individual. In the kit, the cancer is preferably a cancer resistant to a PD-1/PD-L1 signaling inhibitor.

The kit according to the present invention is a kit for treating cancer resistant to a PD-1/PD-L1 signaling inhibitor in an individual. The kit, in one embodiment, comprises a PD-1/PD-L1 signaling inhibitor. The kit is preferably a kit for use in combination with a VEGF signaling inhibitor.

The kit according to the present invention is a kit for treating cancer resistant to a PD-1/PD-L1 signaling inhibitor in an individual. The kit, in one embodiment, comprises a VEGF signaling inhibitor. The kit is preferably a kit for use in combination with a PD-1/PD-L1 signaling inhibitor.

The kit according to the present invention is a kit for treating cancer in which resistance to a PD-1/PD-L1 signaling inhibitor has developed in an individual. The kit, in one embodiment, comprises a VEGF signaling inhibitor and a PD-1/PD-L1 signaling inhibitor.

For any one of the above kits according to the present invention, the PD-1/PD-L1 signaling inhibitor and the VEGF signaling inhibitor may be administered concurrently, separately, or sequentially. In addition, in any one of the above kits according to the present invention, the cancer may be a cancer which has intrinsic resistance or which has acquired resistance or has recurred.

The kit according to the present invention is a kit for treating cancer resistant to a PD-1/PD-L1 signaling inhibitor. The kit, in one embodiment, comprises a PD-1/PD-L1 signaling inhibitor. The kit is preferably a kit for use in combination with a VEGF signaling inhibitor. In the kit, the PD-1/PD-L1 signaling inhibitor and the VEGF signaling inhibitor may be administered concurrently, separately, or sequentially. The kit, in one embodiment, improves the response rate in a group comprising individuals in need of treatment of cancer resistant to a PD-1/PD-L1 signaling inhibitor, as compared with when the PD-1/PD-L1 signaling inhibitor is administered not in combination with the VEGF signaling inhibitor.

The kit according to the present invention is a kit for treating cancer resistant to a PD-1/PD-L1 signaling inhibitor. The kit, in one embodiment, comprises a VEGF signaling inhibitor. The kit is preferably a kit for use in combination with a PD-1/PD-L1 signaling inhibitor. In the kit, the PD-1/PD-L1 signaling inhibitor and the VEGF signaling inhibitor may be administered concurrently, separately, or sequentially. The kit, in one embodiment, improves the response rate in a group comprising individuals in need of treatment of cancer resistant to a PD-1/PD-L1 signaling inhibitor, as compared with when the VEGF signaling inhibitor is administered not in combination with the PD-1/PD-L1 signaling inhibitor.

The kit according to the present invention is a kit for treating cancer resistant to a PD-1/PD-L1 signaling inhibitor. The kit, in one embodiment, comprises a VEGF signaling inhibitor and a PD-1/PD-L1 signaling inhibitor. In the kit, the VEGF signaling inhibitor and the PD-1/PD-L1 signaling inhibitor may be administered concurrently, separately, or sequentially. The kit, in one embodiment, improves the response rate in a group comprising individuals in need of treatment of cancer resistant to a PD-1/PD-L1 signaling inhibitor, as compared with when the PD-1/PD-L1 signaling inhibitor is administered not in combination with the VEGF signaling inhibitor or when the VEGF signaling inhibitor is administered not in combination with the PD-1/PD-L1 signaling inhibitor.

With respect to the above kits according to the present invention, characterized by improvement of the response rate in the group comprising individuals in need of treatment of cancer resistant to a PD-1/PD-L1 signaling inhibitor, in one embodiment, the group comprising individuals in need of treatment of cancer resistant to a PD-1/PD-L1 signaling inhibitor may include an individual not examined for the presence or absence of resistance through diagnosis prior to administration of the PD-1/PD-L1 signaling inhibitor. Alternatively, in another embodiment of the kit, the group comprising individuals in need of treatment of cancer resistant to a PD-1/PD-L1 signaling inhibitor may include an individual who has been examined for the presence or absence of resistance and determined to be resistant through diagnosis prior to administration of the PD-1/PD-L1 signaling inhibitor. In yet another embodiment, the resistance may be resistance caused by conventional treatment comprising a PD-1/PD-L1 signaling inhibitor.

With respect to any one of the above kits according to the present invention, the VEGF signaling inhibitor may be a VEGF antagonist or a VEGFR antagonist.

With respect to any one of the above kits according to the present invention, the VEGF signaling inhibitor may be an anti-VEGF antibody or an anti-VEGFR antibody. In the kit, the anti-VEGF antibody or the anti-VEGFR antibody is preferably bevacizumab, ramucirumab, or aflibercept beta.

With respect to any one of the above kits according to the present invention, the PD-1/PD-L1 signaling inhibitor may be a PD-1 antagonist or a PD-L1 antagonist. In the kit, the PD-1 antagonist may be AMP-224, BMS-936559, MEDI4736, MSB0010718C, MPDL3280A, nivolumab, AMP-514, pembrolizumab (MK-3475), REGN2810, PDR001, BGB-A317, or pidilizumab (CT-011). In the kit, the PD-1 antagonist is preferably an anti-PD-1 antibody, further preferably nivolumab, AMP-514, pembrolizumab (MK-3475), REGN2810, PDR001, BGB-A317, or pidilizumab (CT-011), and more preferably nivolumab or pembrolizumab. Moreover, in the kit, the PD-L1 antagonist may be an anti-PD-L1 antibody. In the kit, the PD-L1 antagonist may be durvalumab, atezolizumab, avelumab, BMS-936559, MSB0010718C, MPDL3280A, or MEDI4736 and is preferably durvalumab, atezolizumab, or avelumab.

Any one of the above kits according to the present invention may be a kit wherein the cancer is selected from a group consisting of breast cancer, liver cancer, lung cancer including small cell lung cancer, ovarian cancer, gastric cancer, bladder cancer, pancreatic cancer, biliary tract cancer, cervical cancer, endometrial cancer, colon cancer, rectal cancer, colorectal cancer, renal cancer, esophageal cancer, prostate cancer, malignant melanoma, head and neck cancer, malignant pleural mesothelioma, glioblastoma, urothelial cancer, soft tissue sarcoma, malignant lymphoma, multiple myeloma, virus-positive solid cancer, virus-negative solid cancer, leukemia, squamous cell carcinoma, Merkel cell carcinoma, pediatric malignant solid tumors, glioma, thyroid cancer, non-small cell lung cancer, Hodgkin's lymphoma, and uterine cancer.

==Treatment Methods According to the Present Invention==

The treatment method according to the present invention is a method for treating cancer in an individual.

The treatment method according to the present invention, in one embodiment, comprises a step of administering, to the individual, a PD-1/PD-L1 signaling inhibitor. In the treatment method, the PD-1/PD-L1 signaling inhibitor is preferably administered in combination with a VEGF signaling inhibitor.

The treatment method according to the present invention, in one embodiment, comprises a step of administering, to the individual, a VEGF signaling inhibitor. In the treatment method, the VEGF signaling inhibitor is preferably administered in combination with a PD-1/PD-L1 signaling inhibitor.

The treatment method according to the present invention, in one embodiment, comprises a step of administering, to the individual, a PD-1/PD-L1 signaling inhibitor and a step of administering a VEGF signaling inhibitor.

In any one of the above treatment methods according to the present invention, the cancer is preferably a cancer resistant to a PD-1/PD-L1 signaling inhibitor.

In any one of the above treatment methods according to the present invention, the PD-1/PD-L1 signaling inhibitor and the VEGF signaling inhibitor may be administered concurrently, separately, or sequentially. In addition, in any one of the above treatment methods according to the present invention, the cancer may be a cancer which has intrinsic resistance or which has acquired resistance or has recurred.

The treatment method according to the present invention is a treatment method for treating cancer resistant to a PD-1/PD-L1 signaling inhibitor. The treatment method, in one embodiment, comprises a step of administering a PD-1/PD-L1 signaling inhibitor. In the treatment method, the PD-1/PD-L1 signaling inhibitor is preferably administered in combination with a VEGF signaling inhibitor. In the treatment method, the PD-1/PD-L1 signaling inhibitor and the VEGF signaling inhibitor may be administered concurrently, separately, or sequentially. The treatment method, in one embodiment, improves the response rate in a group comprising individuals in need of treatment of cancer resistant to a PD-1/PD-L1 signaling inhibitor, as compared with when the PD-1/PD-L1 signaling inhibitor is administered not in combination with the VEGF signaling inhibitor.

The treatment method according to the present invention is a treatment method for treating cancer resistant to a PD-1/PD-L1 signaling inhibitor. The treatment method, in one embodiment, comprises a step of administering a VEGF signaling inhibitor. In the treatment method, the PD-1/PD-L1 signaling inhibitor is preferably administered in combination with a VEGF signaling inhibitor. In the treatment method, the PD-1/PD-L1 signaling inhibitor and the VEGF signaling inhibitor may be administered concurrently, separately, or sequentially. The treatment method, in one embodiment, improves the response rate in a group comprising individuals in need of treatment of cancer resistant to a PD-1/PD-L1 signaling inhibitor, as compared with when the PD-1/PD-L1 signaling inhibitor is administered not in combination with the VEGF signaling inhibitor.

The treatment method according to the present invention is a treatment method for treating cancer resistant to a PD-1/PD-L1 signaling inhibitor. The treatment method, in one embodiment, comprises a step of administering a PD-1/PD-L1 signaling inhibitor and a VEGF signaling inhibitor. In the treatment method, the VEGF signaling inhibitor is preferably administered in combination with a PD-1/PD-L1 signaling inhibitor. In the treatment method, the VEGF signaling inhibitor and the PD-1/PD-L1 signaling inhibitor may be administered concurrently, separately, or sequentially. The treatment method, in one embodiment, improves the response rate in a group comprising individuals in need of treatment of cancer resistant to a PD-1/PD-L1 signaling inhibitor, as compared with when the PD-1/PD-L1 signaling inhibitor is administered not in combination with the VEGF signaling inhibitor or when the VEGF signaling inhibitor is administered not in combination with the PD-1/PD-L1 signaling inhibitor.

With respect to the above treatment methods according to the present invention which improves the response rate in a group comprising individuals in need of treatment of cancer resistant to a PD-1/PD-L1 signaling inhibitor, in one embodiment, the group comprising individuals in need of treatment of cancer resistant to a PD-1/PD-L1 signaling inhibitor may include an individual not examined for the presence or absence of resistance through diagnosis prior to administration of the PD-1/PD-L1 signaling inhibitor. Alternatively, in another embodiment of the treatment method, the group comprising individuals in need of treatment of cancer resistant to a PD-1/PD-L1 signaling inhibitor may include an individual who has been examined for the presence or absence of resistance and determined to be resistant through diagnosis prior to administration of the PD-1/PD-L1 signaling inhibitor. In yet another embodiment, the resistance may be resistance caused by conventional treatment comprising a PD-1/PD-L1 signaling inhibitor.

In any one of the above treatment methods according to the present invention, the VEGF signaling inhibitor may be a VEGF antagonist or a VEGFR antagonist.

In any one of the above treatment methods according to the present invention, the VEGF signaling inhibitor may be an anti-VEGF antibody or an anti-VEGFR antibody. In the treatment method, the anti-VEGF antibody or the anti-VEGFR antibody is preferably bevacizumab, ramucirumab, or aflibercept beta.

In any one of the above treatment methods according to the present invention, the PD-1/PD-L1 signaling inhibitor may be a PD-1 antagonist or a PD-L1 antagonist. In the treatment method, the PD-1 antagonist may be AMP-224, BMS-936559, MEDI4736, MSB0010718C, MPDL3280A, nivolumab, AMP-514, pembrolizumab (MK-3475), REGN2810, PDR001, BGB-A317, or pidilizumab (CT-011). In the treatment, the PD-1 antagonist is preferably an anti-PD-1 antibody, further preferably nivolumab, AMP-514, pembrolizumab (MK-3475), REGN2810, PDR001, BGB-A317, or pidilizumab (CT-011), and more preferably nivolumab or pembrolizumab. Moreover, in the treatment method, the PD-L1 antagonist may be an anti-PD-L1 antibody. In the treatment, the PD-L1 antagonist may be durvalumab, atezolizumab, avelumab, BMS-936559, MSB0010718C, MPDL3280A, or MEDI4736 and is preferably durvalumab, atezolizumab, or avelumab.

In any one of the above treatment methods according to the present invention, the cancer may be selected from a group consisting of breast cancer, liver cancer, lung cancer including small cell lung cancer, ovarian cancer, gastric cancer, bladder cancer, pancreatic cancer, biliary tract cancer, cervical cancer, endometrial cancer, colon cancer, rectal cancer, colorectal cancer, renal cancer, esophageal cancer, prostate cancer, malignant melanoma, head and neck cancer, malignant pleural mesothelioma, glioblastoma, urothelial cancer, soft tissue sarcoma, malignant lymphoma, multiple myeloma, virus-positive solid cancer, virus-negative solid cancer, leukemia, squamous cell carcinoma, Merkel cell carcinoma, pediatric malignant solid tumors, glioma, thyroid cancer, non-small cell lung cancer, Hodgkin's lymphoma, and uterine cancer.

==Uses According to the Present Invention==

The use according to the present invention is a use of a PD-1/PD-L1 signaling inhibitor and/or a VEGF signaling inhibitor for the manufacture of a medicament or kit of the present invention.

In the use according to the present invention, the medicament or kit is a medicament or kit for treating cancer in an individual. In the use, the cancer is preferably a cancer resistant to a PD-1/PD-L1 signaling inhibitor.

In the use according to the present invention, the medicament or kit is a medicament or kit for treating cancer resistant to a PD-1/PD-L1 signaling inhibitor in an individual. In one embodiment of the use, the medicament or kit, in one embodiment, comprises a PD-1/PD-L1 signaling inhibitor. The medicament or kit is preferably a medicament or kit for use in combination with a VEGF signaling inhibitor.

In the use according to the present invention, the medicament or kit is a medicament or kit for treating cancer resistant to a PD-1/PD-L1 signaling inhibitor in an individual. The medicament or kit, in one embodiment, comprises a VEGF signaling inhibitor. The medicament or kit is preferably a medicament or kit for use in combination with a PD-1/PD-L1 signaling inhibitor.

In the use according to the present invention, the medicament or kit is a medicament or kit for treating cancer which has acquired resistance to a PD-1/PD-L1 signaling inhibitor in an individual. The medicament or kit, in one embodiment, comprises a VEGF signaling inhibitor and a PD-1/PD-L1 signaling inhibitor.

In any one of the above uses according to the present invention, the medicament or kit may be a medicament of kit wherein the PD-1/PD-L1 signaling inhibitor and the VEGF signaling inhibitor are administered concurrently, separately, or sequentially. In addition, in any one of the above uses according to the present invention, the cancer may be a cancer which has intrinsic resistance or which has acquired resistance or has recurred.

In the use according to the present invention, the medicament or kit is a medicament or kit for treating cancer resistant to a PD-1/PD-L1 signaling inhibitor. The medicament or kit, in one embodiment, comprises a PD-1/PD-L1 signaling inhibitor. The medicament or kit is preferably a medicament or kit for use in combination with a VEGF signaling inhibitor. In the medicament or kit, the PD-1/PD-L1 signaling inhibitor and the VEGF signaling inhibitor may be administered concurrently, separately, or sequentially. The medicament or kit, in one embodiment, improves the response rate in a group comprising individuals in need of treatment of cancer resistant to a PD-1/PD-L1 signaling inhibitor, as compared with when the PD-1/PD-L1 signaling inhibitor is administered not in combination with the VEGF signaling inhibitor.

In the use according to the present invention, the medicament or kit is a medicament or kit for treating cancer resistant to a PD-1/PD-L1 signaling inhibitor. The medicament or kit, in one embodiment, comprises a VEGF signaling inhibitor. The medicament or kit is preferably a medicament or kit for use in combination with a PD-1/PD-L1 signaling inhibitor. In the medicament or kit, the PD-1/PD-L1 signaling inhibitor and the VEGF signaling inhibitor may be administered concurrently, separately, or sequentially. The medicament or kit, in one embodiment, improves the response rate in a group comprising individuals in need of treatment of cancer resistant to a PD-1/PD-L1 signaling inhibitor, as compared with when the VEGF signaling inhibitor is administered not in combination with the PD-1/PD-L1 signaling inhibitor.

In the use according to the present invention, the medicament or kit is a medicament or kit for treating cancer resistant to a PD-1/PD-L1 signaling inhibitor. The medicament or kit, in one embodiment, comprises a VEGF signaling inhibitor and a PD-1/PD-L1 signaling inhibitor. In the medicament or kit, the VEGF signaling inhibitor and the PD-1/PD-L1 signaling inhibitor may be administered concurrently, separately, or sequentially. The medicament or kit, in one embodiment, improves the response rate in a group comprising individuals in need of treatment of cancer resistant to a PD-1/PD-L1 signaling inhibitor, as compared with when the PD-1/PD-L1 signaling inhibitor is administered not in combination with the VEGF signaling inhibitor or when the VEGF signaling inhibitor is administered not in combination with the PD-1/PD-L1 signaling inhibitor.

With respect to the above uses according to the present invention, characterized by improvement of the response rate in the group comprising individuals in need of treatment of cancer resistant to a PD-1/PD-L1 signaling inhibitor, in one embodiment, the group comprising individuals in need of treatment of cancer resistant to a PD-1/PD-L1 signaling inhibitor may include an individual not examined for the presence or absence of resistance through diagnosis prior to administration of the PD-1/PD-L1 signaling inhibitor. Alternatively, in another embodiment of the medicament or kit, the group comprising individuals in need of treatment of cancer resistant to a PD-1/PD-L1 signaling inhibitor may include an individual who has been examined for the presence or absence of resistance and determined to be resistant through diagnosis prior to administration of the PD-1/PD-L1 signaling inhibitor. In yet another embodiment, the resistance may be resistance caused by conventional treatment comprising a PD-1/PD-L1 signaling inhibitor.

In any one of the above uses according to the present invention, the VEGF signaling inhibitor may be a VEGF antagonist or a VEGFR antagonist.

In any one of the above uses according to the present invention, the VEGF signaling inhibitor may be an anti-VEGF antibody or an anti-VEGFR antibody. In the use, the anti-VEGF antibody or the anti-VEGFR antibody is preferably bevacizumab, ramucirumab, or aflibercept beta.

In any one of the above uses according to the present invention, the PD-1/PD-L1 signaling inhibitor may be a PD-1 antagonist or a PD-L1 antagonist. In the use, the PD-1 antagonist may be AMP-224, BMS-936559, MEDI4736, MSB0010718C, MPDL3280A, nivolumab, AMP-514, pembrolizumab (MK-3475), REGN2810, PDR001, BGB-A317, or pidilizumab (CT-011). In the use, the PD-1 antagonist is preferably an anti-PD-1 antibody, further preferably nivolumab, AMP-514, pembrolizumab (MK-3475), REGN2810, PDR001, BGB-A317, or pidilizumab (CT-011), and more preferably nivolumab or pembrolizumab. Moreover, in the use, the PD-L1 antagonist may be an anti-PD-L1 antibody. In the use, the PD-L1 antagonist may be durvalumab, atezolizumab, avelumab, BMS-936559, MSB0010718C, MPDL3280A, or MEDI4736 and is preferably durvalumab, atezolizumab, or avelumab.

Any one of the above medicaments according to the present invention may be a medicament wherein the cancer is selected from a group consisting of breast cancer, liver cancer, lung cancer including small cell lung cancer, ovarian cancer, gastric cancer, bladder cancer, pancreatic cancer, biliary tract cancer, cervical cancer, endometrial cancer, colon cancer, rectal cancer, colorectal cancer, renal cancer, esophageal cancer, prostate cancer, malignant melanoma, head and neck cancer, malignant pleural mesothelioma, glioblastoma, urothelial cancer, soft tissue sarcoma, malignant lymphoma, multiple myeloma, virus-positive solid cancer, virus-negative solid cancer, leukemia, squamous cell carcinoma, Merkel cell carcinoma, pediatric malignant solid tumors, glioma, thyroid cancer, non-small cell lung cancer, Hodgkin's lymphoma, and uterine cancer.

==VEGF Signaling Inhibitors, PD-1/PD-L1 Signaling Inhibitors, or Combinations Thereof for Use in Cancer Treatment According to the Present Invention==

The VEGF signaling inhibitor according to the present invention is a VEGF signaling inhibitor for use in cancer treatment. The VEGF signaling inhibitor is preferably administered in combination with a PD-1/PD-L1 signaling inhibitor to an individual in need thereof. The VEGF signaling inhibitor is preferably a VEGF signaling inhibitor for use in the treatment of cancer resistant to a PD-1/PD-L1 signaling inhibitor.

The PD-1/PD-L1 signaling inhibitor according to the present invention is a PD-1/PD-L1 signaling inhibitor for use in cancer treatment. The PD-1/PD-L1 signaling inhibitor is preferably administered in combination with a VEGF signaling inhibitor to an individual in need thereof. The PD-1/PD-L1 signaling inhibitor is preferably a PD-1/PD-L1 signaling inhibitor for use in the treatment of cancer resistant to a PD-1/PD-L1 signaling inhibitor.

The combination of a VEGF signaling inhibitor and a PD-1/PD-L1 signaling inhibitor according to the present invention is a combination for use in cancer treatment. The combination is preferably a combination for use in the treatment of cancer resistant to a PD-1/PD-L1 signaling inhibitor.

With respect to any one of the above VEGF signaling inhibitors, PD-1/PD-L1 signaling inhibitors, or combinations according to the present invention, the PD-1/PD-L1 signaling inhibitor and the VEGF signaling inhibitor may be administered concurrently, separately, or sequentially. In addition, in any one of the above VEGF signaling inhibitors, PD-1/PD-L1 signaling inhibitors, or combinations according to the present invention, the cancer may be a cancer which has intrinsic resistance or which has acquired resistance or has recurred.

The VEGF signaling inhibitor, PD-1/PD-L1 signaling inhibitor, or combination according to the present invention is a VEGF signaling inhibitor, PD-1/PD-L1 signaling inhibitor, or combination for treating cancer resistant to a PD-1/PD-L1 signaling inhibitor. The VEGF signaling inhibitor, in one embodiment, is preferably used in combination with a PD-1/PD-L1 signaling inhibitor. The PD-1/PD-L1 signaling inhibitor, in one embodiment, is preferably used in combination with a VEGF signaling inhibitor. In the invention, the PD-1/PD-L1 signaling inhibitor and the VEGF signaling inhibitor may be administered concurrently, separately, or sequentially. The PD-1/PD-L1 signaling inhibitor or combination, in one embodiment, improves the response rate in a group comprising individuals in need of treatment of cancer resistant to a PD-1/PD-L1 signaling inhibitor, as compared with when the PD-1/PD-L1 signaling inhibitor is administered not in combination with the VEGF signaling inhibitor.

The VEGF signaling inhibitor, PD-1/PD-L1 signaling inhibitor, or combination according to the present invention is a VEGF signaling inhibitor, PD-1/PD-L1 signaling inhibitor, or combination for treating cancer resistant to a PD-1/PD-L1 signaling inhibitor. The VEGF signaling inhibitor, in one embodiment, is preferably used in combination with a PD-1/PD-L1 signaling inhibitor. The PD-1/PD-L1 signaling inhibitor, in one embodiment, is preferably used in combination with a VEGF signaling inhibitor. In the invention, the PD-1/PD-L1 signaling inhibitor and the VEGF signaling inhibitor may be administered concurrently, separately, or sequentially. The VEGF signaling inhibitor or combination, in one embodiment, improves the response rate in a group comprising individuals in need of treatment of cancer resistant to a PD-1/PD-L1 signaling inhibitor, as compared with when the VEGF signaling inhibitor is administered not in combination with the PD-1/PD-L1 signaling inhibitor.

The combination according to the present invention is a combination of a VEGF signaling inhibitor and a PD-1/PD-L1 signaling inhibitor for treating cancer resistant to a PD-1/PD-L1 signaling inhibitor. The combination, in one embodiment, comprises a VEGF signaling inhibitor and a PD-1/PD-L1 signaling inhibitor. In the combination, the VEGF signaling inhibitor and the PD-1/PD-L1 signaling inhibitor may be administered concurrently, separately, or sequentially. The combination, in one embodiment, improves the response rate in a group comprising individuals in need of treatment of cancer resistant to a PD-1/PD-L1 signaling inhibitor, as compared with when the PD-1/PD-L1 signaling inhibitor is administered not in combination with the VEGF signaling inhibitor or when the VEGF signaling inhibitor is administered not in combination with the PD-1/PD-L1 signaling inhibitor.

With respect to the above VEGF signaling inhibitors, PD-1/PD-L1 signaling inhibitors, or combinations according to the present invention, the invention being characterized by improvement of the response rate in the group comprising individuals in need of treatment of cancer resistant to a PD-1/PD-L1 signaling inhibitor, in one embodiment, the group comprising individuals in need of treatment of cancer resistant to a PD-1/PD-L1 signaling inhibitor may include an individual not examined for the presence or absence of resistance through diagnosis prior to administration of the PD-1/PD-L1 signaling inhibitor. Alternatively, in another embodiment of the invention, the group comprising individuals in need of treatment of cancer resistant to a PD-1/PD-L1 signaling inhibitor may include an individual who has been examined for the presence or absence of resistance and determined to be resistant through diagnosis prior to administration of the PD-1/PD-L1 signaling inhibitor. In yet another embodiment, the resistance may be resistance caused by conventional treatment comprising a PD-1/PD-L1 signaling inhibitor.

With respect to any one of the above VEGF signaling inhibitors, PD-1/PD-L1 signaling inhibitors, or combinations according to the present invention, the VEGF signaling inhibitor may be a VEGF antagonist or a VEGFR antagonist.

With respect to any one of the above VEGF signaling inhibitors, PD-1/PD-L1 signaling inhibitors, or combinations according to the present invention, the VEGF signaling inhibitor may be a anti-VEGF antibody or an anti-VEGFR antibody. In the medicament, the anti-VEGF antibody or the anti-VEGFR antibody is preferably bevacizumab, ramucirumab, or aflibercept beta.

With respect to any one of the above VEGF signaling inhibitors, PD-1/PD-L1 signaling inhibitors, or combinations according to the present invention, the PD-1/PD-L1 signaling inhibitor may be a PD-1 antagonist or a PD-L1 antagonist. In the invention, the PD-1 antagonist may be AMP-224, BMS-936559, MEDI4736, MSB0010718C, MPDL3280A, nivolumab, AMP-514, pembrolizumab (MK-3475), REGN2810, PDR001, BGB-A317, or pidilizumab (CT-011). In the invention, the PD-1 antagonist is preferably an anti-PD-1 antibody, further preferably nivolumab, AMP-514, pembrolizumab (MK-3475), REGN2810, PDR001, BGB-A317, or pidilizumab (CT-011), and more preferably nivolumab or pembrolizumab. Moreover, in the invention, the PD-L1 antagonist may be an anti-PD-L1 antibody. In the invention, the PD-L1 antagonist may be durvalumab, atezolizumab, avelumab, BMS-936559, MSB0010718C, MPDL3280A, or MEDI4736 and is preferably durvalumab, atezolizumab, or avelumab.

With respect to any one of the above VEGF signaling inhibitors, PD-1/PD-L1 inhibitors, or combinations according to the present invention, the cancer may be selected from a group consisting of breast cancer, liver cancer, lung cancer including small cell lung cancer, ovarian cancer, gastric cancer, bladder cancer, pancreatic cancer, biliary tract cancer, cervical cancer, endometrial cancer, colon cancer, rectal cancer, colorectal cancer, renal cancer, esophageal cancer, prostate cancer, malignant melanoma, head and neck cancer, malignant pleural mesothelioma, glioblastoma, urothelial cancer, soft tissue sarcoma, malignant lymphoma, multiple myeloma, virus-positive solid cancer, virus-negative solid cancer, leukemia, squamous cell carcinoma, Merkel cell carcinoma, pediatric malignant solid tumors, glioma, thyroid cancer, non-small cell lung cancer, Hodgkin's lymphoma, and uterine cancer.

One embodiment of the present invention is a medicament for treating cancer in an individual. In the medicament of the present embodiment, a PD-1/PD-L1 signaling inhibitor and a VEGF signaling inhibitor are administered in combination.

One embodiment of the present invention is a medicament comprising a PD-1/PD-L1 signaling inhibitor. The medicament of the present embodiment is administered in combination with a VEGF signaling inhibitor, for treating cancer, to an individual in need thereof.

One embodiment of the present invention is a medicament comprising a VEGF signaling inhibitor. The medicament of the present embodiment is administered in combination with a PD-1/PD-L1 signaling inhibitor, for treating cancer, to an individual in need thereof.

One embodiment of the present invention is a medicament comprising a VEGF signaling inhibitor and a PD-1/PD-L1 signaling inhibitor and is administered to an individual in need thereof for treating cancer.

One embodiment of the present invention is a medicament comprising a PD-1/PD-L1 signaling inhibitor or a VEGF signaling inhibitor and improves the response rate in a group comprising individuals in need of cancer treatment, as compared with a control group. In the present embodiment, the medicament is a medicament comprising a PD-1/PD-L1 signaling inhibitor and may be for use in combination with a VEGF signaling inhibitor. In this case, the medicament improves the response rate in the group as compared with when the PD-1/PD-L1 signaling inhibitor is administered not in combination with the VEGF signaling inhibitor. In another embodiment, the medicament is a medicament comprising a VEGF signaling inhibitor and may be for use in combination with a PD-1/PD-L1 signaling inhibitor. In this case, the medicament improves the response rate in the group as compared with when the VEGF signaling inhibitor is administered not in combination with the PD-1/PD-L1 signaling inhibitor.

One embodiment of the present invention is a kit for treating cancer, comprising a VEGF signaling inhibitor and/or a PD-1/PD-L1 signaling inhibitor.

The medicaments and kits of the present invention, other than the VEGF signaling inhibitor and PD-1/PD-L1 signaling inhibitor, can be used in combination with another additional medicament etc. for treating cancer or with a known therapy such as radiotherapy or surgery.

The medicaments and kits of the present invention include embodiments of medicaments or kits in which the PD-1/PD-L1 signaling inhibitor and/or VEGF signaling inhibitor, which are active ingredients, are formulated into a single formulation (combination drug) or embodiments of medicaments or kits comprising two or more separately formulated formulations.

The treatment method according to the present invention is a treatment method for treating cancer in an individual in need thereof. The treatment method comprises a step of administering, to an individual, one or more of the medicaments and kits and VEGF signaling inhibitors, PD-1/PD-L1 signaling inhibitors, and combinations thereof of the present invention in the respective embodiment described herein.

The treatment method of the present invention may include a step of treating with another medicament, agent, or kit etc. for treating cancer, other than the medicaments and kits and VEGF signaling inhibitors, PD-1/PD-L1 signaling inhibitors, and combinations thereof of the present invention specifically described herein, or a step of carrying out a known therapy such as radiotherapy or surgery. The other medicament may include one or more chemotherapeutic agents.

The use of the present invention is a use of a PD-1/PD-L1 signaling inhibitor and/or a VEGF signaling inhibitor for the manufacture of a medicament or kit of the present invention. The use of the present invention, other than the PD-1/PD-L1 signaling inhibitor and/or the VEGF signaling inhibitor, may include use of another agent for treating cancer or a known therapy such as radiotherapy or surgery. The other agent may include one or more chemotherapeutic agents.

The VEGF signaling inhibitor of the present invention is a VEGF signaling inhibitor for use in cancer treatment. The VEGF signaling inhibitor is preferably administered in combination with a PD-1/PD-L1 signaling inhibitor to an individual in need thereof. The VEGF signaling inhibitor of the present invention, other than the PD-1/PD-L1 signaling inhibitor, can be used in combination with another additional medicament, agent, or kit etc. for treating cancer or with a known therapy such as radiotherapy or surgery.

The PD-1/PD-L1 signaling inhibitor of the present invention is a PD-1/PD-L1 signaling inhibitor for use in cancer treatment. The PD-1/PD-L1 signaling inhibitor is preferably administered in combination with a VEGF signaling inhibitor to an individual in need thereof. The PD-1/PD-L1 signaling inhibitor of the present invention, other than the VEGF signaling inhibitor, can be used in combination with another additional medicament, agent, or kit etc. for treating cancer or with a known therapy such as radiotherapy or surgery.

The combination of the present invention is a combination of a VEGF signaling inhibitor and a PD-1/PD-L1 signaling inhibitor, for use in cancer treatment. The combination of the present invention, other than the VEGF signaling inhibitor and the PD-1/PD-L1 signaling inhibitor, can be used in combination with another additional medicament, agent, or kit etc. for treating cancer or with a known therapy such as radiotherapy or surgery.

The PD-1/PD-L1 signaling inhibitor and the VEGF signaling inhibitor, administered in combination to an individual having a cancer, provide a higher effect, i.e., synergistic effect, compared with the individual and separate usage of the VEGF signaling inhibitor or PD-1/PD-L1 signaling inhibitor. Thus, in the medicaments, treatment methods, kits, and uses and VEGF signaling inhibitors, PD-1/PD-L1 signaling inhibitors, and combinations thereof according to the present invention (hereinafter also referred to as the "medicaments etc. of the present invention" or "medicaments etc. according to the present invention"), embodiments in which the VEGF signaling inhibitor and the PD-1/PD-L1 signaling inhibitor are administered in combination are preferred.

Here, in the medicaments, kits, treatment methods, uses, VEGF signaling inhibitors, PD-1/PD-L1 signaling inhibitors, and combinations of the present invention, chemotherapeutic agents that can be administered in combination with the VEGF signaling inhibitor and PD-1/PD-L1 signaling inhibitor are, for example, publicly known or novel anticancer substances for the cancer to the treated. More specifically, they can be, for example, erlotinib, capecitabine, calcium levofolinate, calcium folinate, carboplatin, cyclophosphamide, cisplatin, docetaxel, nedaplatin, paclitaxel, pirarubicin, fluorouracil (5-FU), bleomycin, mitomycin C, tegafur-uracil formulation, tegafur-gimeracil-oteracil potassium formulation, tegafur, aclarubicin, amrubicin, ifosfamide, irinotecan hydrochloride hydrate, topotecan, etoposide, crizotinib, gemcitabine hydrochloride, cytarabine, doxorubicin, nimustine, temozolomide, nogitecan hydrochloride, pemetrexed sodium hydrate, everolimus, epirubicin, exemestane, goserelin, tamoxifen, dexamethasone, doxifluridine, toremifene, vinorelbine, pirarubicin, prednisolone, methotrexate, lapatinib, mepitiostane, mitoxantrone, medroxyprogesterone, leuprorelin, letrozole, octreotide, vindesine, and teceleukin, but are not limited thereto.

The types of chemotherapeutic agents that can be administered in combination with the VEGF signaling inhibitor and PD-1/PD-L1 signaling inhibitor can be selected, as appropriate, by a person skilled in the art according to the type of cancer to be treated, the therapeutic effect, the patient's condition, tolerance, and the types of VEGF signaling inhibitor and PD-1/PD-L1 signaling inhibitor. However, where bevacizumab is used as the VEGF signaling inhibitor and atezolizumab is used as the PD-1/PD-L1 signaling inhibitor, the chemotherapeutic agent is preferably carboplatin, docetaxel, paclitaxel, etoposide, capecitabine, oxaliplatin, fluorouracil, calcium levofolinate, calcium folinate, irinotecan hydrochloride hydrate, gemcitabine hydrochloride, cisplatin, temozolomide, or nogitecan hydrochloride, or a combination thereof, and is more preferably carboplatin and/or paclitaxel.

Where a PD-1/PD-L1 signaling inhibitor or a VEGF signaling inhibitor is individually and separately administered to a cancer, a valid anti-cancer effect is obtained when the cancer is responsive to each of these agents. Furthermore, as shown in the examples, administering a PD-1/PD-L1 signaling inhibitor and a VEGF signaling inhibitor in combination to a cancer responsive to each of these agents is recognized to have a significantly higher anti-cancer effect, i.e., synergistic effect, than each of the anti-cancer effects obtained by administering the PD-1/PD-L1 signaling inhibitor or the VEGF signaling inhibitor. Accordingly, with the medicaments etc. of the present invention, a cancer treatment combining a PD-1/PD-L1 signaling inhibitor and a VEGF signaling inhibitor is more effective than one using the PD-1/PD-L1 signaling inhibitor and the VEGF signaling inhibitor individually and separately. Thus, in the medicaments and kits and the VEGF signaling inhibitors, PD-1/PD-L1 signaling inhibitors, and combinations thereof of the present invention, the cancer is preferably treated with a combination of the PD-1/PD-L1 signaling inhibitor and the VEGF signaling inhibitor.

Furthermore, in cases where the cancer is unresponsive to a PD-1/PD-L1 signaling inhibitor, treating with a PD-1/PD-L1 signaling inhibitor has a significantly low or completely or almost no observable anti-cancer effect as compared with cancer which is responsive to a PD-1/PD-L1 signaling inhibitor. However, using a PD-1/PD-L1 signaling inhibitor and a VEGF signaling inhibitor in combination on a cancer unresponsive to a PD-1/PD-L1 signaling inhibitor is recognized to have a significantly higher anti-cancer effect than when the VEGF signaling inhibitor is used not in combination with the PD-1/PD-L1 signaling inhibitor. The effect obtained by the combination is naturally significantly higher than when the PD-1/PD-L1 signaling inhibitor is used not in combination with the VEGF signaling inhibitor. As such, the medicaments etc. of the present invention exhibit efficacies thereof particularly in the treatment of cancer unresponsive to a PD-1/PD-L1 signaling inhibitor and for which treatment is difficult.

As above, the medicaments etc. of the present invention, by using a PD-1/PD-L1 signaling inhibitor and a VEGF signaling inhibitor in combination, provide a significantly higher anti-cancer effect, i.e., synergistic effect, than when the PD-1/PD-L1 signaling inhibitor or the VEGF signaling inhibitor is used individually and separately, whether the cancer is responsive or unresponsive to a PD-1/PD-L1 signaling inhibitor.

Thus, the treatment of cancer with the medicaments etc. of the present invention, combining a PD-1/PD-L1 signaling inhibitor and a VEGF signaling inhibitor, in a group comprising individuals in need of cancer treatment produces a higher anti-cancer effect in each individual in the group as compared with a control group not treated as such. Here, the control group is a group comprising individuals in need of cancer treatment and may be either a group administered with neither the PD-1/PD-L1 signaling inhibitor nor the VEGF signaling inhibitor, a group administered with the PD-1/PD-L1 signaling inhibitor not in combination with the VEGF signaling inhibitor, or a group administered with the VEGF signaling inhibitor not in combination with the PD-1/PD-L1 signaling inhibitor.

For example, where the medicament of the present invention is a medicament comprising a PD-1/PD-L1 signaling inhibitor, for use in combination with a VEGF signaling inhibitor, a higher anti-cancer effect is achieved in each individual in a group which is an assembly comprising individuals in need of cancer treatment, as compared with when the PD-1/PD-L1 signaling inhibitor is administered not in combination with the VEGF signaling inhibitor. For example, where the medicament of the present invention is a medicament comprising a VEGF signaling inhibitor, for use in combination with a PD-1/PD-L1 signaling inhibitor, a higher anti-cancer effect is achieved in each individual in a group which is an assembly comprising individuals in need of cancer treatment, as compared with when the VEGF signaling inhibitor is administered not in combination with the PD-1/PD-L1 signaling inhibitor.

As already explained, the medicaments etc. of the present invention, by treating with a combination of a PD-1/PD-L1 signaling inhibitor and a VEGF signaling inhibitor, are also effective on cancer unresponsive to a PD-1/PD-L1 signaling inhibitor. Consequently, where the above "group" (assembly comprising individuals in need of cancer treatment) is an assembly of individuals with cancer unresponsive to a PD-1/PD-L1 signaling inhibitors, the efficacies of the medicaments etc. of the present invention are particularly exhibited. The medicaments etc. of the present invention, when used in a group comprising individuals with cancer unresponsive to a PD-1/PD-L1 signaling inhibitor, can increase the proportion of individuals in which an anti-cancer effect is recognized, i.e., improve the response rate, as compared with when the PD-1/PD-L1 signaling inhibitor or the VEGF signaling inhibitor is separately used. Additionally, the unresponsiveness is not particularly limited so long as it is an unresponsiveness or resistance to a PD-1/PD-L1 signaling inhibitor and may be an intrinsic resistance or an unresponsiveness in cancer which has acquired resistance or has recurred. In one embodiment, the group comprising individuals in need of cancer treatment comprises an individual who has been determined to be resistant. In another embodiment, the group comprising individuals in need of cancer treatment comprises an individual who has been determined to have acquired resistance by conventional treatment. In the present embodiment, for example, the medicament may be a medicament comprising a PD-1/PD-L1 signaling inhibitor, for use in combination with a VEGF signaling inhibitor, or a medicament comprising a VEGF signaling inhibitor, for use in combination with a PD-1/PD-L1 signaling inhibitor.

In one embodiment, the group comprising individuals in need of cancer treatment may be a group comprising an individual who has not been determined as to the presence or absence of cancer unresponsiveness to a PD-1/PD-L1 signaling inhibitor prior to treatment with a combination of a PD-1/PD-L1 signaling inhibitor and a VEGF signaling inhibitor. In one embodiment, for at least some of the individuals in the group comprising individuals in need of cancer treatment, the presence or absence of cancer unresponsiveness to a PD-1/PD-L1 signaling inhibitor may be determined prior to treatment with a combination of a PD-1/PD-L1 signaling inhibitor and a VEGF signaling inhibitor. The unresponsiveness is not particularly limited so long as it is an unresponsiveness or resistance to a PD-1/PD-L1 signaling inhibitor and may be an intrinsic resistance. As mentioned above, in cases where the cancer is unresponsive to a PD-1/PD-L1 signaling inhibitor, the efficacies of the medicaments etc. of the present invention are particularly exhibited and can thus improve the response rate in a group comprising individuals in need of cancer treatment.

The method for determining the presence or absence of cancer resistance to a PD-1/PD-L1 signaling inhibitor is not limited provided that determination can be made. However, for example, determination can be made based on the presence or absence of markers, by detecting such markers as genes, proteins or histological features specifically expressed in cancer with such a resistance in a cancer tissue collected prior to treatment. Those skilled in the art can arbitrarily select a genetic or histological method for determination from among known methods.

Here, the cancer to be treated by the medicaments etc. of the present invention is not limited provided that the medicaments etc. of the present invention are effective. However, for example, it may be selected from a group consisting of breast cancer, liver cancer, lung cancer including small cell lung cancer, ovarian cancer, gastric cancer, bladder cancer, pancreatic cancer, biliary tract cancer, cervical cancer, endometrial cancer, colon cancer, rectal cancer, colorectal cancer, renal cancer, esophageal cancer, prostate cancer, malignant melanoma, head and neck cancer, malignant pleural mesothelioma, glioblastoma, urothelial cancer, soft tissue sarcoma, malignant lymphoma, multiple myeloma, virus-positive solid cancer, virus-negative solid cancer, leukemia, squamous cell carcinoma, Merkel cell carcinoma, pediatric malignant solid tumors, glioma, thyroid cancer, non-small cell lung cancer, Hodgkin's lymphoma, and uterine cancer.

The medicaments etc. of the present invention, by using a PD-1/PD-L1 signaling inhibitor and a VEGF signaling inhibitor in combination, provide a significantly higher anti-cancer effect than when the PD-1/PD-L1 signaling inhibitor or the VEGF signaling inhibitor is used individually and separately, whether the cancer is responsive or unresponsive to a PD-1/PD-L1 signaling inhibitor. However, since the present invention can exhibit an efficacy particularly in the treatment of cancer which is unresponsive to a PD-1/PD-L1 signaling inhibitor and for which treatment is difficult, it is particularly effective in the treatment of individuals who are resistant or unresponsive to a conventional treatment, cancer unsuitable for continuation of a conventional treatment, or cancer not exhibiting a desired level of responsiveness to a conventional treatment (for example, due to unresponsiveness and/or toxicity), i.e., cancer for which treatment is difficult, such as cancer with intrinsic resistance to a PD-1/PD-L1 signaling inhibitor, cancer with acquired resistance acquired from a conventional treatment with a PD-1/PD-L1 signaling inhibitor etc., or cancer which has recurred after a conventional treatment with a PD-1/PD-L1 signaling inhibitor etc. In particular, the medicaments etc. of the present invention are particularly effective on cancer for which treatment is difficult due to unresponsiveness to a PD-1/PD-L1 signaling inhibitor. Even for cancer unresponsive to a PD-1/PD-L1 signaling inhibitor, i.e., cancer with intrinsic resistance to a PD-1/PD-L1 signaling inhibitor, cancer with acquired resistance due to an already performed conventional treatment, or cancer which has recurred, the combination of a VEGF signaling inhibitor and a PD-1/PD-L1 signaling inhibitor provides a high effect, i.e., synergistic effect, and significantly improves the cancer treatment effect, as compared with when the PD-1/PD-L1 signaling inhibitor and the VEGF signaling inhibitor are individually and separately administered. Moreover, the medicaments etc. of the present invention are, for example, useful in the treatment of cancers which are not surgically resectable, progressive, and/or have recurred. The medicaments etc. of the present invention preferably can be used for the treatment of progressive or recurrent cancer not requiring curative resection, non-resectable progressive or recurrent cancer, or inoperable or recurrent cancer.

Herein, the terms "resistance", "unresponsiveness", and "tolerance" are used synonymously and are not limited so long as they are states in which a cell or an individual lacks responsiveness (also referred to as sensitivity) and/or the ability to produce a significant response (for example, a partial response and/or a complete response) is reduced. For example, a cancer resistant to a PD-1/PD-L1 signaling inhibitor is a cancer without any responsiveness or a cancer not displaying a significant response, such as a partial response or a complete response, to a treatment using a PD-1/PD-L1 signaling inhibitor. If an agent is administered to a cancer with "resistance" or "unresponsiveness" thereto, not only will desired effects not be obtained, sometimes the cancer may even further progress or turn into a cancer with a higher grade of malignancy. The "resistance" or "unresponsiveness" may be an "intrinsic resistance" or an "acquired resistance".

Herein, the term "intrinsic resistance" refers to an intrinsic unresponsiveness of a cell or an individual to an agent. When a cell or an individual has intrinsic resistance to an agent, the agent does not work or works poorly as compared with a lack of resistance (i.e., when there is sensitivity or responsiveness). Whatever the drug treatment, none achieves 100% response rate, and there are always non-responders, people for which the drug does not work. The response rates of medicaments for asthma, cancer, depression, diabetes, peptic ulcer, hyperlipidemia, etc. are generally said to be at a percentage of tens.

Herein, the term "acquired resistance" refers to an unresponsiveness acquired subsequent to an exposure to an agent although the cell or the individual had intrinsic responsiveness (or sensitivity) to the agent. Due to acquired resistance, an agent that initially worked does not work during administration or works poorly, as compared with a lack of resistance (i.e., when there is responsiveness). In particular, the acquired resistance in the medicaments etc. of the present invention may be a resistance that developed after a conventional treatment. For example, anti-angiogenic therapeutic agents are generally used in many cancer treatments including liver cancer. However, even if the agents are effective in the initial stage of the treatment, resistance sometimes develop upon continuation of repeated treatments. For example, a cancer resistant to a PD-1/PD-L1 signaling inhibitor is a cancer that no longer regresses or even progresses in the presence of a PD-1/PD-L1 signaling inhibitor.

Herein, the term "recurrence" refers to the observation of cancer reappearance or regrowth after the cancer was once cured or shrunk with treatment. Even when a treatment appears to have gone well, "recurrence" occurs when the cancer, incompletely removed by surgery and so small as to be invisible, reappears or when the cancer, once shrunk by pharmacotherapy (anti-cancer therapy) or radiotherapy, becomes large again. With "recurrence", the same cancer can appear near or at the same site as the treated cancer, though the same cancer can also appear in an organ or member separate from that of the treated cancer. The appearance of the same cancer in an organ or member separated from that of the treated cancer is called "metastasis" in particular. Cancer cells enter the blood vessels and the lymph and riding on the blood or lymph stream, move to another organ or member, where they proliferate. Cancer often metastasizes to sites where blood flow is abundant, such as lymph nodes, lungs, liver, brain, and bones. In the case of a cancer that appeared due to recurrence, the individual with the cancer has experienced a conventional treatment, such as pharmacotherapy or radiotherapy. Thus, the cancer that appeared due to recurrence may be a cancer with acquired resistance to the conventional treatment.

The unresponsiveness and/or responsiveness to a treatment can be assessed using a method known in the field and is not limited provided that a desired assessment can be made. For example, unresponsiveness and/or responsiveness may be assessed by an in vivo or in vitro assay on the proliferation of disease-derived cells towards a treatment (for example, a treatment with an agent). The acquisition of unresponsiveness, maintenance of responsiveness, and/or an increase in non-responders may be assessed by an in vivo or in vitro assay etc. on the proliferation of disease-derived cells. In one embodiment, unresponsiveness can be represented by a change in $IC_{50}$ or $EC_{50}$ or a decreased proliferation of disease-derived cells. In one embodiment, the change is greater than any one of about 50%, 100%, and/or 200%. In addition, the change in unresponsiveness and/or responsiveness, for example, can be assessed in vivo by evaluating the response to treatment, the duration of the response, and/or the progression-free survival, e.g., partial response and complete response. The change in unresponsiveness and/or responsiveness may be based on a change in the response to treatment, the duration of the response and/or the progression-free survival, e.g., the number of partial responses and/or complete responses, in a population of individuals.

In one embodiment of the present invention, the cancer to be treated by the medicaments etc. of the present invention may be a cancer which has progressed when subjected to a conventional treatment, during treatment, or after treatment. For example, the cancer may be a cancer that has progressed after having received a conventional treatment. For example, the cancer progressed in any one of about 1, 2, 3, 4, 5, 6, 7, 8, 9, 10, 11, or 12 months after initiation of the conventional treatment. In another embodiment, for example, the cancer progressed in any one of about 3, 6, 9, or 12 months after initiation of the conventional treatment. In one embodiment of the present invention, the cancer is resistant or unresponsive to a conventional treatment. In another embodiment, the cancer is recurrent. That is, the cancer is initially responsive to a conventional treatment but recurs at the primary lesion or a metastatic cancer develops in any one of about 6, 7, 8, 9, 10, 11, 12, 24, or 36 months following discontinuation of the conventional treatment.

In the present invention, the conventional treatment comprises the administration of a PD-1/PD-L1 signaling inhibitor. In another embodiment, the conventional treatment is a monotherapy of a PD-1 antagonist or a PD-L1 antagonist. In another embodiment, the conventional treatment is a monotherapy of a PD-1 antagonist or a PD-L1 antagonist. In another embodiment, the conventional treatment comprises the administration of a PD-1/PD-L1 signaling inhibitor and a chemotherapeutic agent. In another embodiment, the conventional treatment comprises the administration of a PD-1 antagonist and a chemotherapeutic agent. In another embodiment, the conventional treatment comprises the administration of a PD-L1 antagonist and a chemotherapeutic agent. In another embodiment, the conventional treatment comprises the administration of a PD-1 antagonist and a taxane. In another embodiment, the administration of a PD-L1 antagonist and a taxane is included. In another embodiment, the conventional treatment comprises the administration of a PD-L1 antagonist and Nab-paclitaxel. In another embodiment, the conventional treatment comprises the administration of a PD-L1 antagonist and 5-FU. In another embodiment, the conventional treatment comprises the administration of a PD-L1 antagonist and a topoisomerase inhibitor. The conventional treatment comprises the administration of a PD-L1 antagonist and a topoisomerase inhibitor. In another embodiment, the conventional treatment comprises the administration of a PD-L1 antagonist and irinotecan hydrochloride hydrate or topotecan. In another embodiment, the conventional treatment comprises the administration of a PD-L1 antagonist, erlotinib, capecitabine, and/or 5-FU. In another embodiment, the conventional treatment comprises the administration of a PD-1 antagonist and an anti-CTLA4 antibody. In another embodiment, the conventional treatment comprises the administration of a PD-L1 antagonist and an anti-CTLA4 antibody. In another embodiment, the conventional treatment comprises the administration of an anti-CTLA4 antibody. In another embodiment, the conventional treatment is a neoadjuvant therapy of a PD-L1 antagonist.

In one embodiment of the present invention, the taxane is paclitaxel. In another embodiment, albumin is human serum albumin. In another embodiment, a nanoparticle comprises paclitaxel coated with albumin. In another embodiment, the average particle size of nanoparticles in a nanoparticle composition is about 200 nm or less (less than about 200 nm). In another embodiment, the composition comprises a nanoparticle formulation (Nab-paclitaxel (which is interchangeably used with the term "ABRAXANE (Registered Trademark)")) of paclitaxel stabilized with albumin. In another embodiment, the composition is Nab-paclitaxel (ABRAXANE (Registered Trademark)).

Herein, "using in combination" or "combined use" of a VEGF signaling inhibitor and a PD-1/PD-L1 signaling inhibitor includes concurrent administration using separate formulations or a single pharmaceutical formulation and separate or sequential administration in any order, preferably within a period in which both (or all) active agents concurrently exhibit biological activities. The order of administration, frequency of administration, administration time, etc. of the VEGF signaling inhibitor and the PD-1/PD-L1 signaling inhibitor can be optionally determined by those skilled in the art. Either one of the VEGF signaling inhibitor and the PD-1/PD-L1 signaling inhibitor may be administered before or after the other or they may be concurrently administered. In another embodiment, another agent or another medicament other than the VEGF signaling inhibitor and the PD-1/PD-L1 signaling inhibitor may be used concurrently with the VEGF signaling inhibitor and the PD-1/PD-L1 signaling inhibitor or before or after each inhibitor. In another embodiment, radiotherapy or surgery may be performed concurrently with the VEGF signaling inhibitor and the PD-/PD-L1 signaling inhibitor or before or after each inhibitor.

Herein, "treatment", "treat", or "treating" (also referred to as "therapy", "apply therapy", or "applying therapy") means the reduction, alleviation, or mitigation of a certain disease or symptom and includes the protection (prevention) from the development of a future disease or symptom and the suppression of progression. Desirable therapeutic effects of a treatment include symptom remission, decreasing any direct or indirect pathological result of the disease, decreasing the rate of symptom progression, recovering or alleviating the disease state, and improved prognosis. The "treatment" or "therapy" is not limited to a "treatment" or "therapy" which necessarily achieves complete recovery or cures the disease or symptom as a result thereof, nor is it limited to the obtainment of desirable therapeutic effects, i.e., effective "treatment" or "therapy". For example, cancer treatment (or treatment for cancer) means dosing or carrying out surgery, radiotherapy, etc. on a subject with cancer or diagnosed with cancer, for the purpose of achieving at least one desirable therapeutic effect, such as reducing the number of cancer cells, shrinking the tumor size, decreasing the rate of cancer cells infiltrating peripheral organs, or decreasing tumor metastasis or tumor growth rate. In one embodiment of the present invention, cancer treatment refers to treating with a medicament, kit, or treatment method of the present invention.

The therapeutic effects, i.e., efficacy, of a treatment for cancer can be assessed by the methods or criteria illustrated herein or by one or more known methods or criteria (see W. A. Weber, *J. Nucl. Med.* 50:1S-10S (2009)). For example, with respect to the inhibition of tumor growth, a T/C of 42% or less is the lowest level of anti-tumor activity by the U.S. National Cancer Institute (NCI) standards. A T/C of <10% is regarded as a high anti-tumor activity level, where T/C (%)=median tumor volume of those who received treatment/median tumor volume of control×100.

In one embodiment, the therapeutic effects, i.e., efficacy of the anti-cancer effect, of a treatment for cancer can be assessed by one or more known criteria for the state of the patient, affected organ, or affected cell etc. Examples of the criteria include partial response (PR), complete response (CR), overall response rate (ORR), disease control rate (DCR), progression-free survival (PFS), disease-free survival (DFS), overall survival (OS), pathological complete response (pCR), and clinical complete response (cCR) etc.

ORR refers to the proportion of people showing shrinkage or reduced volume of cancer size for a minimum time period. Moreover, ORR can be expressed as the sum of complete response rate and partial response rate. DCR refers to the proportion of patients without disease progression and can be expressed by the sum of complete response rate, partial response rate, and stable disease rate (SD). PFS, also called "time to tumor progression", refers to the length of time during treatment and after treatment in which a patient lives without cancer progression and includes the period in which the patient experienced CR or PR and the period in which the patient experienced SD. DFS is the length of time during treatment and after treatment in which a patient lives without recurrence or other diseases. OS is the period in which a subject lived starting from the date of treatment commencement. Prolonging OS by treatment is, for example, prolonging the point estimation of a median survival from the date of trial commencement in a group of patients receiving the treatment as compared with a group of untreated patients.

In one embodiment, the response to a treatment with a medicament, kit, or treatment method of the present invention is any one of PR, CR, PFS, DFS, ORR, DCR, or OS assessed using the response criteria in Response Evaluation Criteria in Solid Tumours (RECIST) 1.1.

In one embodiment, a specific effect evaluation marker can be used to assess the efficacy of a treatment for cancer. The serum CA19-9 (carbohydrate antigen 19-9) level in an individual administered with a composition comprising nanoparticles comprising a PD-1/PD-L1 signaling inhibitor and albumin is reduced at least about 50% (such as at least any one of about 60%, 70%, 80%, 90%, 95%, etc.) as compared with the serum CA19-9 level before the treatment.

Not all the embodiments of the present invention are effective in achieving a desirable therapeutic effect in all subjects. However, any one of the embodiments of the present invention should achieve a desirable therapeutic effect in a statistically significant number of subjects determined by any statistical test known in the technical field, such as Student's t-test, chi-squared test, U test according to Mann-Whitney, Kruskal-Wallis test (H test), Jonckheere-Terpstra test, and Wilcoxon test.

Among the criteria illustrated herein or known criteria for assessing therapeutic effects on cancer, a treatment can be determined to be effective or have an anti-cancer effect if efficacy is recognized by at least one criterion. It is preferred that the efficacy is associated with prolonged survival of the patient or with improvement of systemic symptoms, such as an improvement in pain. However, the treatment can also be determined to be effective when there are therapeutic effects such as shrinkage or temporary disappearance of the cancer. Moreover, "more effective", "high efficacy", "high therapeutic effect", or "elevated therapeutic effect", etc. compared with a subject for comparison means a higher effectiveness, by comparison, with respect to at least one criterion among the criteria shown here or the known criteria.

The PD-1/PD-L1 signaling inhibitor can be any agent capable of inhibiting the function or activity of PD-1 or PD-L1 by a direct or indirect effect and may be a PD-1 antagonist or a PD-L1 antagonist. The PD-1/PD-L1 signaling inhibitor may be an inhibitor which inhibits the function or activity of PD-1 or a PD-L1 inhibitor which inhibits the function or activity of PD-L1.

The PD-1 antagonist can be any molecule capable of neutralizing, blocking, inhibiting, suppressing, reducing, or interfering the function or activity of PD-1 or PD-L1. For example, it may be an anti-PD-1 antibody or an antigen-binding fragment thereof or a PD-L1 molecule or a derivative thereof which inhibits the binding of PD-1 and PD-L1 by binding to PD-1. Examples thereof can include antibodies, antibody fragments, binding polypeptides, peptides, and non-peptide molecules. More specifically, examples of the PD-1 antagonist can include AMP-224, BMS-936559, MEDI4736, MSB0010718C, MPDL3280A, nivolumab, AMP-514, pembrolizumab (MK-3475), REGN2810, PDR001, BGB-A317, and pidilizumab (CT-011). The PD-1 antagonist is preferably an anti-PD-1 antibody or an antigen-binding fragment thereof and is further preferably a PD-1 neutralizing antibody or an antigen-binding fragment thereof.

An anti-PD-1 antibody is an antibody that binds to PD-1, preferably an antibody which binds to PD-1 and inhibits the function thereof, further preferably an antibody which inhibits the binding of PD-1 or B7.1 to PD-L1 to inhibit the function thereof, and more preferably an antibody which inhibits the signaling induced by the binding of PD-1 or B7.1 to PD-L1, e.g., a neutralizing antibody.

Inhibiting the function of PD-1 refers to releasing the suppression of T cell activation induced as a consequence of PD-1 or B7.1 binding to PD-L1, and the activity of PD-1, compared with the activity in the control, is reduced at least 5%, 10%, 20%, 30%, 40%, 50%, 60%, 70%, 80%, 90%, or 100%. The activity of PD-1 is determined by any standard method (including those described herein) in the field.

As the PD-1 antagonist, for example, nivolumab, AMP-514, pembrolizumab (MK-3475), REGN2810, PDR001, BGB-A317, or pidilizumab (CT-011) can be used, but it is preferable to use nivolumab or pembrolizumab.

Considering the desired function, the anti-PD-1 antibody can be any antibody having the same antigen binding properties as nivolumab, AMP-514, pembrolizumab, REGN2810, PDR001, BGB-A317, or pidilizumab. For example, it may be an antibody or an antigen-binding fragment thereof comprising hypervariable regions (CDRs) each having an amino acid sequence identical to the amino acid sequence of each CDR in the respective heavy chain and light chain of nivolumab, AMP-514, pembrolizumab, REGN2810, PDR001, BGB-A317, or pidilizumab. Alternatively, considering the desired function, the anti-PD-1 antibody may be an antibody or an antigen-binding fragment thereof comprising an amino acid sequence of the heavy chain variable (HV) region or light chain variable (LV) region having an amino acid sequence identical to the amino acid sequence of the respective HV region or LV region of nivolumab, AMP-514, pembrolizumab, REGN2810, PDR001, BGB-A317, or pidilizumab.

In one embodiment, the anti-PD-1 antibody may be an antibody or an antigen-binding fragment thereof comprising an amino acid sequence having at least 80%, 85%, 90%, 95%, 98%, or 99% sequence identity to the respective amino acid sequence of nivolumab, AMP-514, pembrolizumab, REGN2810, PDR001, BGB-A317, or pidilizumab. In one embodiment, the anti-PD-1 antibody may be an antibody or an antigen-binding fragment thereof comprising CDRs each comprising an amino acid sequence having at least 80%, 85%, 90%, 95%, 98%, or 99% sequence identity to the amino acid sequence of each CDR in the respective heavy chain and light chain of nivolumab, AMP-514, pembrolizumab, REGN2810, PDR001, BGB-A317, or pidilizumab. In one embodiment, the anti-PD-1 antibody may be an antibody or an antigen-binding fragment thereof comprising a HV region and a LV region comprising amino acid sequences having at least 80%, 85%, 90%, 95%, 98%, or 99% sequence identity to the respective amino acid sequences of the HV region and LV region of nivolumab, AMP-514, pembrolizumab, REGN2810, PDR001, BGB-A317, or pidilizumab.

The PD-L1 antagonist can be any molecule capable of neutralizing, blocking, inhibiting, suppressing, reducing, or interfering the function or activity of PD-L1 or PD-1. For example, it may be an anti-PD-L1 antibody or an antigen-binding fragment thereof or a PD-1 molecule or a derivative thereof which inhibits the binding of PD-1 and PD-L1 by binding to PD-L1. Examples thereof can include antibodies, antibody fragments, binding polypeptides, peptides, and non-peptide molecules. The PD-L1 antagonist is preferably an anti-PD-L1 antibody or an antigen-binding fragment thereof and is further preferably a PD-L1 neutralizing antibody or an antigen-binding fragment thereof.

An anti-PD-L1 antibody is an antibody that binds to PD-L1, preferably an antibody which binds to PD-L1 and inhibits the function thereof, further preferably an antibody which inhibits the binding of PD-1 or B7.1 to PD-L1 to inhibit the function thereof, and more preferably an antibody which inhibits the signaling induced by the binding of PD-1 or B7.1 to PD-L1, e.g., a neutralizing antibody.

Inhibiting the function of PD-L1 refers to releasing the suppression of T cell activation induced as a consequence of PD-1 or B7.1 binding to PD-L1, and the activity of PD-L1, compared with the activity in the control, is reduced at least 5%, 10%, 20%, 30%, 40%, 50%, 60%, 70%, 80%, 90%, or 100%. The activity of PD-L1 is determined by any standard method (including those described herein) in the field.

As the anti-PD-L1 antibody, for example, any one or more antibodies of atezolizumab, avelumab (MSB0010718C), durvalumab, BMS-936559, MPDL3280A, MEDI4736, KN035, CX-072, LY3300054, and FAZ053 can be used. However, it is preferable to use atezolizumab, avelumab, durvalumab, BMS-936559, MPDL3280A, or MEDI4736, and it is further preferable to use atezolizumab, avelumab, or durvalumab.

Considering the desired function, the anti-PD-L1 antibody can be any antibody having the same antigen binding properties as atezolizumab, avelumab, durvalumab, BMS-936559, MPDL3280A, MEDI4736, KN035, CX-072, LY3300054, or FAZ053. For example, it may be an antibody comprising CDR sequences each having an amino acid sequence identical to the amino acid sequence (SEQ ID NOs: 5-10) of each hypervariable region (HCDR1-3, LCDR1-3) in the heavy chain (SEQ ID NO: 1) and light chain (SEQ ID NO: 2) of atezolizumab, an antibody comprising CDR sequences each having an amino acid sequence identical to the amino acid sequence (SEQ ID NOs: 15-20) of each hypervariable region (HCDR1-3, LCDR1-3) in the heavy chain (SEQ ID NO: 11) and light chain (SEQ ID NO: 12) of avelumab, an antibody comprising CDR sequences each having an amino acid sequence identical to the amino acid sequence of each hypervariable region (HCDR1-3, LCDR1-3) in the heavy chain (SEQ ID NO: 21) and light chain (SEQ ID NO: 22) of durvalumab, an antibody comprising CDR sequences each having an amino acid sequence identical to the amino acid sequence (SEQ ID NO: 27-29) of each hypervariable region (HCDR1-3) in the heavy chain (SEQ ID NO: 25) of KN035, an antibody comprising CDR sequences each having an amino acid sequence identical to the amino acid sequence of each hypervariable region (HCDR1-3, LCDR1-3) in the heavy chain (SEQ ID NO: 30) and light chain (SEQ ID NO: 31) of CX-072, or an antibody comprising CDR sequences each having an amino acid sequence identical to the amino acid sequence (SEQ ID NOs: 38-43) of each hypervariable region (HCDR1-3, LCDR1-3) in the heavy chain (SEQ ID NO: 34) and light chain (SEQ ID NO: 35) of LY3300054, or an antigen-binding fragment thereof. Alternatively, it may be an antibody or an antigen-binding fragment, comprising hypervariable regions (CDRs) each having an amino acid sequence identical to the amino acid sequence of each CDR in the respective heavy chain and light chain of BMS-936559, MPDL3280A, MEDI4736, or FAZ053.

Alternatively, considering the desired function, the anti-PD-L1 antibody may be an antibody or an antigen-binding fragment thereof, comprising a heavy chain variable (VH) region and/or a light chain variable (VL) region having an amino acid sequence identical to the amino acid sequence of the VH region (SEQ ID NO: 3) and/or the VL region (SEQ ID NO: 4) of atezolizumab, the VH region (SEQ ID NO: 13) and/or the VL region (SEQ ID NO: 14) of avelumab, the VH region (SEQ ID NO: 23) and or the VL region (SEQ ID NO: 24) of durvalumab, the VH region (SEQ ID NO: 26) of KN035, the VH region (SEQ ID NO: 32) and/or the VL region (SEQ ID NO: 33) of CX-072, or the VH region (SEQ ID NO: 36) and/or the VL region (SEQ ID NO: 37) of LY3300054. Alternatively, it may be an antibody or an antigen-binding fragment thereof, comprising a heavy chain variable (VH) region and/or light chain variable (VL) region having an amino acid sequence identical to the amino acid sequence of the respective VH region and/or VL region of BMS-936559, MPDL3280A, MEDI4736, or FAZ053.

In one embodiment, the anti-PD-L1 antibody may be an antibody or an antigen-binding fragment thereof comprising amino acids having at least 80%, 85%, 90%, 95%, 98%, or 99% sequence identity to the respective amino acid sequence of atezolizumab, avelumab, durvalumab, BMS-936559, MPDL3280A, MEDI4736, KN035, CX-072, LY3300054, or FAZ053. In one embodiment, the anti-PD-L1 antibody may be an antibody or an antigen-binding fragment thereof comprising CDRs each comprising an amino acid sequence having at least 80%, 85%, 90%, 95%, 98%, or 99% sequence identity to the amino acid sequence of each CDR in the respective heavy chain and light chain of atezolizumab, avelumab, durvalumab, BMS-936559, MPDL3280A, MEDI4736, KN035, CX-072, LY3300054, or FAZ053. In one embodiment, the anti-PD-L1 antibody may be an antibody or an antigen-binding fragment thereof comprising a VH region and a VL region comprising amino acid sequences having at least 80%, 85%, 90%, 95%, 98%, or 99% sequence identity to the respective amino acid sequences of the respective VH region and VL region in atezolizumab, avelumab, durvalumab, BMS-936559, MPDL3280A, MEDI4736, KN035, CX-072, LY3300054, or FAZ053.

The VEGF signaling inhibitor can be any agent capable of inhibiting the function or activity of VEGF signaling by a direct or indirect effect and may be a VEGF antagonist or a VEGFR antagonist. The VEGF signaling inhibitor may be a VEGF inhibitor which inhibits the function or activity of VEGF or a VEGF receptor (VEGFR) inhibitor which inhibits the function of VEGFR.

The VEGF antagonist can be any molecule capable of neutralizing, blocking, inhibiting, suppressing, reducing, or interfering the function or activity of VEGF or VEGF receptor (VEGFR) and may be an anti-VEGF antibody or an anti-VEGF receptor (VEGFR) antibody, or an antigen-binding fragment thereof. Additionally, for example, it may be a VEGF molecule or a derivative thereof which inhibits the binding of VEGF and VEGFR by binding to VEGFR. Examples of the VEGF antagonist can include antibodies, antibody fragments, binding polypeptides, peptides, and non-peptide molecules. The VEGF antagonist is preferably an anti-VEGF antibody or an anti-VEGFR antibody, or an antigen-binding fragment thereof and is further preferably a VEGF neutralizing antibody or a VEGFR neutralizing antibody, or an antigen-binding fragment thereof.

VEGF neutralizing antibodies and VEGFR neutralizing antibodies are antibodies that reduce or eliminate the function or activity of VEGF and VEGFR respectively, neutralizing the function or activity thereof. However, VEGF and VEGFR has a ligand-receptor relation, so a VEGF neutralizing antibody and a VEGFR neutralizing antibody both may be an anti-VEGF antibody or an anti-VEGFR antibody which binds to VEGF or VEGFR and inhibits the binding of VEGF and VEGFR.

By inhibiting the function of VEGF or VEGFR, the activity of VEGF or VEGFR, compared with the activity in the control, is reduced at least 5%, 10%, 20%, 30%, 40%, 50%, 60%, 70%, 80%, 90%, or 100%. The activity of VEGF or VEGFR is determined by any standard method (including those described herein) in the field.

As the anti-VEGF antibody or anti-VEGFR antibody, bevacizumab, ramucirumab, or aflibercept beta can be preferably used.

Considering the desired function, the anti-VEGF antibody or anti-VEGFR antibody can be any antibody having the same antigen binding specificity as bevacizumab, ramucirumab, or aflibercept beta. For example, it may be an antibody comprising CDR sequences each having an amino acid sequence identical to the amino acid sequence (SEQ ID NOs: 48-53) of each hypervariable region (HCDR1-3, LCDR1-3) in the heavy chain (SEQ ID NO: 44) and light chain (SEQ ID NO: 45) of bevacizumab or an antibody comprising CDR sequences each having an amino acid sequence identical to the amino acid sequence (SEQ ID NO: 58-63) of each hypervariable region (HCDR1-3, LCDR1-3) in the heavy chain (SEQ ID NO: 54) and light chain (SEQ ID NO: 55) of ramucirumab, or an antigen-binding fragment thereof. Alternatively, it may be an antibody or an antigen-binding fragment thereof, comprising CDRs each having an amino acid sequence identical to the amino acid sequence of each hypervariable region (CDR) in the heavy chain and light chain of aflibercept beta.

Alternatively, considering the desired function, the anti-VEGF antibody or anti-VEGFR antibody may be an antibody or an antigen-binding fragment thereof, comprising a heavy chain variable (VH) region and/or a light chain variable (VL) region having an amino acid sequence identical to the amino acid sequence of the VH region (SEQ ID NO: 46) and/or the VL region (SEQ ID NO: 47) of bevacizumab or the VH region (SEQ ID NO: 56) and/or the VL region (SEQ ID NO: 57) of ramucirumab. Alternatively, it may be an antibody or an antigen-binding fragment thereof, comprising a heavy chain variable (VH) region and/or a light chain variable (VL) region having an amino acid sequence identical to the amino acid sequence of the VH region and/or the VL region of aflibercept beta.

In one embodiment, the anti-VEGF antibody or anti-VEGFR antibody may be an antibody or an antigen-binding fragment thereof comprising amino acids having at least 80%, 85%, 90%, 95%, 98%, or 99% sequence identity to the respective amino acid sequence of bevacizumab, ramucirumab, or aflibercept beta. In one embodiment, the anti-VEGF antibody or anti-VEGFR antibody may be an antibody or an antigen-binding fragment thereof comprising CDRs each comprising an amino acid sequence having at least 80%, 85%, 90%, 95%, 98%, or 99% sequence identity to the amino acid sequence of each CDR in the respective heavy chain and light chain of bevacizumab, ramucirumab, or aflibercept beta. In one embodiment, the anti-VEGF antibody or anti-VEGFR antibody may be an antibody or an antigen-binding fragment thereof comprising a heavy chain variable (VH) region and a light chain variable (VL) region comprising amino acid sequences having at least 80%, 85%, 90%, 95%, 98%, or 99% sequence identity to the respective amino acid sequences of the respective VH region and VL region in bevacizumab, ramucirumab, or aflibercept beta.

In the medicaments, treatment methods, kits, and use and the VEGF signaling inhibitors, PD-1/PD-L1 signaling inhibitors, and combinations thereof of the present invention, embodiments of combinations of a VEGF signaling inhibitor and a PD-1/PD-L1 signaling inhibitor include, for example, the following but are not limited thereto:

Bevacizumab and AMP-224 combination, bevacizumab and BMS-936559 combination, bevacizumab and MEDI4736 combination, bevacizumab and MSB0010718C combination, bevacizumab and MPDL3280A combination, bevacizumab and nivolumab combination, bevacizumab and AMP-514 combination, bevacizumab and pembrolizumab (MK-3475) combination, bevacizumab and REGN2810 combination, bevacizumab and PDR001 combination, bevacizumab and BGB-A317 combination, or bevacizumab and pidilizumab (CT-011) combination.

Ramucirumab and AMP-224 combination, ramucirumab and BMS-936559 combination, ramucirumab and MEDI4736 combination, ramucirumab and MSB0010718C combination, ramucirumab and MPDL3280A combination, ramucirumab and nivolumab combination, ramucirumab and AMP-514 combination, ramucirumab and pembrolizumab (MK-3475) combination, ramucirumab and REGN2810 combination, ramucirumab and PDR001 combination, ramucirumab and BGB-A317 combination, or ramucirumab and pidilizumab (CT-011) combination.

Aflibercept beta and AMP-224 combination, aflibercept beta and BMS-936559 combination, aflibercept beta and MEDI4736 combination, aflibercept beta and MSB0010718C combination, aflibercept beta and MPDL3280A combination, aflibercept beta and nivolumab combination, aflibercept beta and AMP-514 combination, aflibercept beta and pembrolizumab (MK-3475) combination, aflibercept beta and REGN2810 combination, aflibercept beta and PDR001 combination, aflibercept beta and BGB-A317 combination, or aflibercept beta and pidilizumab (CT-011) combination.

Bevacizumab and atezolizumab combination, bevacizumab and avelumab (MSB0010718C) combination, bevacizumab and durvalumab combination, bevacizumab and BMS-936559 combination, bevacizumab and MPDL3280A combination, bevacizumab and MEDI4736 combination, bevacizumab and KN035 combination, bevacizumab and CX-072 combination, bevacizumab and LY3300054 combination, or bevacizumab and FAZ053 combination.

Ramucirumab and atezolizumab combination, ramucirumab and avelumab (MSB0010718C) combination, ramucirumab and durvalumab combination, ramucirumab and BMS-936559 combination, ramucirumab and MPDL3280A combination, ramucirumab and MEDI4736 combination, ramucirumab and KN035 combination, ramucirumab and CX-072 combination, ramucirumab and LY3300054 combination, or ramucirumab and FAZ053 combination.

Aflibercept beta and atezolizumab combination, aflibercept beta and avelumab (MSB0010718C) combination, aflibercept beta and durvalumab combination, aflibercept beta and BMS-936559 combination, aflibercept beta and MPDL3280A combination, aflibercept beta and MEDI4736 combination, aflibercept beta and KN035 combination, aflibercept beta and CX-072 combination, aflibercept beta and LY3300054 combination, or aflibercept beta and FAZ053 combination.

The antibodies can be obtained as polyclonal antibodies or monoclonal antibodies using known means. While the antibody origin is not limited, the antibodies are preferably of mammalian origin, more preferably of human origin. Monoclonal antibodies of mammalian origin include those produced by hybridomas and those produced by hosts transformed with expression vectors comprising antibody genes with genetic engineering techniques. The antibodies may be chimeric antibodies, humanized antibodies, or human antibodies, or antibodies derived from libraries or antibody fragments thereof.

The antibodies may be conjugated antibodies linked to various molecules such as polyethylene glycol (PEG), radioactive substances, or toxins. Such conjugated antibodies can be obtained by chemically modifying obtained antibodies. In addition, methods for modifying antibodies have already been established in this field. The "antibodies" herein also include these conjugated antibodies.

The antibodies include not only bivalent antibodies represented by IgG but also monovalent antibodies or multivalent antibodies represented by IgM. The multivalent antibodies of the present invention include multivalent antibodies having completely the same antigen-binding site or multivalent antibodies having partially or completely different antigen-binding sites.

Further, the antibodies may be bispecific antibodies. A bispecific antibody refers to an antibody which has, in the same antibody molecule, variable regions that recognize different epitopes, but the epitopes may exist in different molecules or within the same molecule.

Methods for producing bispecific antibodies are known. For example, a bispecific antibody can be made by linking two types of antibodies that recognize different antigens. The antibodies to be linked may each be a half molecule of an antibody having an H chain and an L chain or a quarter molecule of an antibody consisting of only an H chain. Alternatively, a fusion cell producing a bispecific antibody can be made by fusing hybridomas that produce different monoclonal antibodies. Furthermore, a bispecific antibody can be made with genetic engineering techniques.

The antibodies may be low molecular weight antibodies. A low molecular weight antibody comprises an antibody fragment lacking a portion of the full-length antibody. Partial deletions of antibody molecules are allowed so long as the antibody molecules bind to Arid5A. The antibody fragments in the present invention preferably comprise either one or both of a heavy chain variable region (VH) and a light chain variable region (VL). The amino acid sequence of VH or VL can comprise an addition, deletion, and/or substitution. Furthermore, the molecules can lack a portion of either one or both of VH and VL so long as they bind to PD-L1. Additionally, the antibody fragments may be chimerized or humanized. Specific examples of the antibody fragment can include, for example, Fab, Fab', F(ab')2, and Fv. Moreover, specific examples of the low molecular weight antibody can include, for example, Fab, Fab', F(ab')2, Fv, scFv, diabody, and sc(Fv)2.

Formulations can be made into tablets, granules, powders, capsules, emulsions, suspensions, or syrups or injections such as sterile solutions or liquid suspensions according to conventional means. When these active ingredients have been separately formulated into two or more formulations, the individual formulations can be concurrently administered or separately or sequentially administered with a set time interval apart. The two or more formulations can also be respectively administered at different frequencies in a day. The medicament according to the present invention can be orally or parenterally administered, systemically or topically. When these active ingredients have been separately formulated into two or more formulations, the individual formulations can also be administered by different routes.

Where the medicament according to the present invention is prepared as a plurality of different formulations which are likely to be administered concurrently or at a specific interval, for example, documents such as package inserts or sales brochures for commercially available medicaments can indicate the respective combined use thereof. Additionally, it is possible to prepare a kit comprising formulations respectively containing the foregoing.

The formulation can be prepared for storage by mixing a desired active ingredient with an optional pharmaceutically acceptable carrier, excipient, or stabilizer in the form of a lyophilized formulation or an aqueous solution.

Examples of pharmaceutically acceptable materials can include sterile water, physiological saline, stabilizers, excipients, buffers, preservatives, surfactants, chelators (such as EDTA), binders, etc.

The surfactant can be a non-ionic surfactant. Typical examples thereof can include those with HLB6-18, such as soribitan fatty acid esters such as sorbitan monocaprylate, sorbitan monolaurate, and sorbitan monopalmitate; glycerin fatty acid esters such as glycerin monocaprylate, glycerin monomyristate, and glycerin monostearate; etc.

The surfactant can also be an anionic surfactant. Typical examples thereof can include alkyl sulfates having a $C_{10-18}$ alkyl group, such as sodium acetyl sulfate, sodium lauryl sulfate, and sodium oleyl sulfate; polyoxyethylene alkylether sulfates with a $C_{10-18}$ alkyl group and an average number of moles added of ethylene oxide of 2-4, such as sodium polyoxyethylene lauryl sulfate; alkyl sulfosuccinates having a $C_{8-18}$ alkyl group, such as sodium lauryl sulfosuccinate; natural surfactants, e.g., lecithin and glycerophospholipids; sphingophospholipids such as sphingomyelin; and sucrose fatty acid esters with a $C_{12-18}$ fatty acid.

Examples of buffers can include phosphoric acid, citric acid buffers, acetic acid, malic acid, tartaric acid, succinic acid, lactic acid, potassium phosphate, gluconic acid, caprylic acid, deoxycholic acid, salicylic acid, triethanolamine, fumaric acid, other organic acids, etc., or carbonic acid buffers, tris buffers, histidine buffers, imidazole buffers, etc.

In addition, solution formulations may be prepared by dissolving in aqueous buffers known in the field of solution formulations. The buffer concentration is generally 1-500 mM, preferably 5-100 mM, and further preferably 10-20 mM.

Examples of carbohydrates or saccharides such as polysaccharides and monosaccharides can include dextran, glucose, fructose, lactose, xylose, mannose, maltose, sucrose, trehalose, raffinose, etc.

Examples of sugar alcohols can include mannitol, sorbitol, inositol, etc.

When the formulation is an aqueous solution, examples thereof include physiological saline and isotonic solutions containing glucose or other adjuvants, such as D-sorbitol, D-mannose, D-mannitol, and sodium chloride, and may be used in combination with appropriate solubilizing agents, such as alcohols (ethanol, etc.), polyalcohols (propylene glycol, PEG, etc.), nonionic surfactants (polysorbate 80, HCO-50), etc.

A diluent, solubilizing agent, pH adjuster, analgesic, sulfur-containing reducing agent, antioxidant, etc. may be further included as desired.

As one embodiment, administration by gene therapy may be included in addition to administering the VEGF signaling inhibitor and the PD-1/PD-L1 signaling inhibitor through a conventional route. For example, the use in gene therapy of the anti-VEGF antibody, the anti-PD-1 antibody, or the anti-PD-L1 antibody can be carried out using a known method.

The dose and dosing schedule of the medicament of the present invention differ with the subject to be administered, the age and body weight of the subject, the disease condition, the administration method, and the type of VEGF signaling inhibitor and PD-1/PD-L1 signaling inhibitor to be used, etc., and they can be empirically determined by a person skilled in the art according to the manufacturer's instructions.

In the medicaments etc. of the present invention, the VEGF signaling inhibitor and the PD-1/PD-L1 signaling inhibitor are preferably administered in combination and may be administered concurrently, separately, or sequentially. The VEGF signaling inhibitor and the PD-1/PD-L1 signaling inhibitor can be administered as individual formulations concurrently, or separately or sequentially with a set time interval apart. The two or more formulations may be respectively administered at different frequencies in a day, and they can be respectively administered at different frequencies with a certain number of days apart. Each formulation may be administered to one subject at separate dosing schedules as illustrated below.

The VEGF signaling inhibitor, for example, can be administered, by intravenous infusion, to a human subject at about 1 mg/kg to about 50 mg/kg per administration or about 4 mg/kg to about 15 mg/kg per administration. More specifically, it can be administered at about 4 mg/kg (body weight), about 5 mg/kg (body weight), about 8 mg/kg (body weight), about 7.5 mg/kg (body weight), about 10 mg/kg (body weight), or about 15 mg/kg (body weight) per administration. In addition, these doses can be given, for example, at a dosing interval of about a week or about more than a week, a dosing interval of about two weeks or about more than two weeks, or a dosing interval of about three weeks or about more than three weeks. Moreover, while the duration of each administration is preferably about 30 minutes to about 90 minutes, it is not limited thereto so long as administration can be carried out safely.

As mentioned above, specific examples of the VEGF signaling inhibitor include the anti-VEGF antibody bevacizumab, ramucirumab, or aflibercept beta. As mentioned above, the dose and dosing schedule of the VEGF signaling inhibitor can be determined by a person skilled in the art according to the embodiment thereof. However, for example, in the case of bevacizumab, administration can be made to a human subject at about 5 mg/kg (body weight) or about 10 mg/kg (body weight) per administration at a dosing interval of about two weeks or more than two weeks, at a dose of about 7.5 mg/kg (body weight) per administration at a dosing interval of about three weeks or more than three weeks, or at about 15 mg/kg (body weight) per administration at a dosing interval of about three weeks or more than three weeks. In the case of ramucirumab, administration can be made to a human subject at about 8 mg/kg (body weight) per administration at a dosing interval of about two weeks or at about 10 mg/kg (body weight) per administration at a dosing interval of about three weeks. In the case of aflibercept beta, administration can be made at about 4 mg/kg (body weight) per administration at a dosing interval of about two weeks.

Moreover, the PD-1/PD-L1 signaling inhibitor, for example, can be administered, by intravenous infusion, to a human subject at a dose of about 0.1 mg to about 30,000 mg per administration. Further specifically, administration can be made at about 1 mg or more and about 10 mg or less, about 80 mg or less, about 240 mg or less, about 840 mg or less, about 1,000 mg or less, or about 1,200 mg/or less per administration. More specifically, administration can be made at about 10 mg, about 80 mg, about 240 mg, about 840 mg, or about 1,200 mg per administration. Alternatively, administration can be made at about 1.0 mg/kg (body weight) or more, about 2.0 mg/kg (body weight) or more, about 2.5 mg/kg (body weight) or more, about 10 mg/kg (body weight) or more, or about 20 mg/kg (body weight) or more, and about 100 mg/kg (body weight) or less per administration. More specifically, administration can be made at about 2 mg/kg (body weight), about 10 mg/kg (body weight), about 15 mg/kg (body weight), or about 20 mg/kg (body weight) per administration. In addition, these doses can be given, for example, at a dosing interval of about two weeks or about more than two weeks or a dosing interval of about three weeks or about more than three weeks. Moreover, while the duration of each administration is preferably about 30 minutes to about 90 minutes, it is not limited thereto so long as administration can be carried out safely.

As mentioned above, the dose and dosing schedule of the PD-1/PD-L1 signaling inhibitor can be determined by a person skilled in the art according to the embodiment thereof. However, for example, in the case of atezolizumab, administration can be made to a human subject at a dose of about 1,200 mg per administration at a dosing interval of about one week or more, preferably at a dosing interval of about two to four weeks, and more preferably at a dosing interval of about three weeks. Alternatively, in the case of atezolizumab, administration can be made at a dose of about 840 mg per administration at a dosing interval of about one week or more, preferably at a dosing interval of about two weeks. In the case of avelumab, administration can be made at about 10 mg/kg (body weight) per administration at a dosing interval of about three weeks. In the case of durvalumab, administration can be made at a dose of about 10 mg/kg (body weight) per administration at a dosing interval of about two weeks. In the case of nivolumab, administration can be made at about 240 mg per administration at a dosing interval of about two weeks or at about 80 mg per administration at a dosing interval of about three weeks. In the case of pembrolizumab, administration can be made at about 2 mg/kg (body weight) per administration at a dosing interval of about three weeks or at about 200 mg per administration at a dosing interval of about three weeks.

In the medicaments etc. of the present invention, the VEGF signaling inhibitor and the PD-1/PD-L1 signaling inhibitor are administered in combination. However, for example, where bevacizumab is used as the VEGF signaling inhibitor and atezolizumab is used as the PD-1/PD-L1 signaling inhibitor, a dosing schedule as illustrated below can be used. Atezolizumab is intravenously administered, then after at least about five minutes, bevacizumab is intravenously administered. Alternatively, where the subject is in a poor physical condition following the intravenous administration of atezolizumab, the administration is followed by a period of about 60 minutes±15 minutes, after which bevacizumab is intravenously administered.

With respect to the administration of the VEGF signaling inhibitor and the PD-1/PD-L1 signaling inhibitor, a person skilled in the art can adjust, as appropriate, the administration time, dosing interval, number of doses, and administration period according to the therapeutic effect, the patient's condition, tolerance, etc.

In the medicaments, etc. of the present invention, the VEGF signaling inhibitor and the PD-1/PD-L1 signaling inhibitor are administered in combination, and one or more chemotherapeutic agent may be further administered in combination therewith. For example, when bevacizumab is used as the VEGF signaling inhibitor and atezolizumab is used as the PD-1/PD-L1 signaling inhibitor, the chemotherapeutic agent is preferably carboplatin, docetaxel, paclitaxel, etoposide, capecitabine, oxaliplatin, fluorouracil, calcium levofolinate, calcium folinate, irinotecan hydrochloride hydrate, gemcitabine hydrochloride, cisplatin, temozolomide, or nogitecan hydrochloride, or a combination thereof, and is more preferably carboplatin and/or paclitaxel. In that case, a person skilled in the art can adjust, as appropriate, the administration time, dosing interval, number of doses, and administration period of the VEGF signaling inhibitor, the PD-1/PD-L1 signaling inhibitor and one or more chemotherapeutic agent according to the therapeutic effect, the patient's condition, tolerance, etc.

For example, for a human subject, administration may be made at about 5 mg/kg (body weight), about 10 mg/kg (body weight), about 7.5 mg/kg (body weight), or about 15 mg/kg (body weight) per administration in the case of bevacizumab, and at about 1,200 mg or 840 mg per administration in the case of atezolizumab. Moreover, with the combination of bevacizumab and atezolizumab, for example, carboplatin may be administered at about AUC6 per administration, docetaxel may be administered at about 75 mg/m$^2$ per administration, paclitaxel may be administered at about 200 mg/m$^2$ (i.v.) per administration, Nab-paclitaxel may be administered at about 100 mg/m$^2$ (i.v.) per administration, and/or etoposide may be administered at about 100 mg/m$^2$ per administration, and administration may be made with carboplatin at about AUC6 per administration and paclitaxel at about 200 mg/m$^2$ (i.v.) per administration.

The agents may be administered concurrently, separately, or sequentially at a dosing interval of about one to four weeks respectively. For example, bevacizumab may be administered at about 5 mg/kg (body weight) per administration at a dosing interval of about two weeks, at about 10 mg/kg (body weight) per administration at a dosing interval of about two weeks, at about 7.5 mg/kg (body weight) per administration at a dosing interval of about three weeks, or at about 15 mg/kg (body weight) per administration at a dosing interval of about three weeks.

For example, atezolizumab may be administered at about 1,200 mg per administration at a dosing interval of about three weeks or at 840 mg per administration at a dosing interval of about two weeks.

Additionally, "about", when used to modify a numerically defined parameter (e.g., the dosage of an agent or the length of time of treatment used in the combination therapy described herein), means that the parameter varies within a range of 10% above or below the numerical value given for the parameter. For example, "about 5 mg" means "4.5 mg to 5.5 mg".

Incorporation by Reference

All publications, patents, and patent applications mentioned herein are hereby incorporated by reference in their entireties, as if each individual publication, patent, or patent application were specifically and individually indicated to be incorporated by reference. In case of conflict, the present application, including definitions herein, will control.

EXAMPLES

The present invention will be more specifically explained using the examples below, but the present invention is not limited by these examples.

==Making of Mouse Models==

OV2944-HM-1 cells and Colon 38 cells were cultured using cell culture flasks in an incubator (set at 37° C. and 5% CO$_2$). In the case of OV2944-HM-1 cells, the cells were collected, resuspended at $1\times10^7$ cells/mL, and subcutaneously inoculated ($1\times10^6$ cells/mouse) in the inguinal region on the right of B6C3F1 mice (CLEA Japan, Inc.). In the case of Colon 38 cells, the cells were collected, resuspended at $2\times10^7$ cells/mL, mixed with equal volume of Matrigel (Nippon Becton, Dickinson and Company), and subcutaneously inoculated ($1\times10^6$ cells/mouse) in the inguinal region on the right of C57BL/6 mice (Charles River Laboratories Japan). After palpable tumors were established, the animals were randomized into test groups such that the groups each have a similar average tumor volume at the beginning of the test.

==Immunohistochemistry==

For immunohistochemistry, an anti-mouse CD8α monoclonal antibody (clone KT15, GeneTex) was used for detecting CD8 protein, an anti-mouse B7-H1/PD-L1 polyclonal antibody (R&D Systems) was used for detecting PD-L1 protein, and an anti-mouse granzyme B antibody (clone GB11) was used for detecting granzyme B.

Example 1

Characterization of a syngenic mouse model using the mouse ovarian cancer cell line OV2944-HM-1 and mouse colorectal cancer cell line Colon 38 and anti-tumor activity by the combined use of an anti-PD-L1 antibody and an anti-VEGF antibody ==Treatment Method==

The day of randomization was the day on which administration of the agents began, 5 mg/kg of an anti-mouse PD-L1 antibody (clone 6E11, WO 2015/095418) was intraperitoneally administered twice a week, and 10 mg/kg of an anti-mouse VEGF antibody (clone B20-4.1.1) was intraperitoneally administered once a week. Mouse IgG was administered at the same dose as the control for each antibody.

==Intratumoral PD-L1 Protein and CD8 Protein Expression==

For the OV2944-HM-1 cancer bearing mice and Colon 38 cancer bearing mice, paraffin sections were made from tumors extracted on the day of randomization (unadministered), and PD-L1 protein and CD8 protein expression was detected in the tumor tissues using immunohistochemistry.

The tumor tissues (HM-1) of the OV2944-HM-1 cancer bearing mice, compared with the tumor tissues (Colon 38) of Colon 38 cancer bearing mice, had low PD-L1 protein and CD8 protein expression levels and exhibited an immune desert-like phenotype (FIG. 1).

==Tumor Volume==

On days 1, 4, 8, 11, 15, 19, 23, and 25 after initiation of administration, the tumor volume was measured using calipers, and a statistical analysis was performed using the tumor volume on the last day of the test. When OV2944-HM-1 cells were used, compared with the control group, a significant difference was not observed in the anti-PD-L1 antibody single administration group, and there was a significant decrease in the anti-VEGF antibody single administration group. Compared with each single administration group, the group with combined use of both antibodies (combined use) showed a significant decrease in tumor volume (FIG. 2A). When Colon 38 cells were used, compared with the tumor volume of the control group, both the anti-PD-L1 antibody single administration group and the anti-VEGF antibody single administration group showed a significant decrease. Compared with each single administration group, the group with combined use of both antibodies (combined use) showed a significant decrease in tumor volume (FIG. 2B).

In other words, the tumors in the OV2944-HM-1 cancer bearing mice were unresponsive to the anti-PD-L1 antibody, which is a PD-1/PD-L1 signaling inhibitor, but the combined use of the anti-PD-L1 antibody and the anti-VEGF antibody, which is a VEGF signaling inhibitor, significantly inhibited tumor growth compared with the control group (mouse IgG), the anti-VEGF antibody single administration group, and the anti-PD-L1 antibody single administration group respectively. The above demonstrated that the combined use of an anti-PD-L1 antibody and an- anti-VEGF antibody produced a stronger anti-tumor effect than each antibody alone whether there was resistance or sensitivity to the anti-PD-L1 antibody alone.

Example 2

Effect on intratumoral CD8-positive T cells and contribution to the anti-tumor effect of the combined use of an anti-PD-L1 antibody and an anti-VEGF antibody in OV2944-HM-1 cancer bearing mice.

==Treatment Method==

The day of randomization was the day on which administration of the agents began, 5 mg/kg of 6E11 antibody was intraperitoneally administered to the OV2944-HM-1 cancer bearing mice twice a week, and 10 mg/kg of B20-4.1.1 was intraperitoneally administered once a week. Moreover, an anti-mouse CD8 antibody (clone 116-13.1) was intraperitoneally administered to the OV2944-HM-1 cancer bearing mice at 100 µg/mouse twice a week from 11 days before the day of randomization. Mouse IgG was administered at the same dose as the control for each antibody.

==CD8-Positive T Cells and Granzyme B-Positive CD8-Positive T Cells==

On day 8 after initiation of administration, tumors were extracted from the mice, and cells dispersed with gentleMACS (Registered Trademark), Octo Dissociator were quantified for granzyme B-positive T cells and CD8-positive Tcells in the tumor tissues by flow cytometry using an anti-mouse Granzyme B antibody(clone GB11)-Alexa647 (BD Biosciences) and an anti-mouse CD8α antibody (clone 53-6.3)-BV650 (BD Biosciences).

Moreover, paraffin sections of the tumors extracted on day 8 after initiation of administration were prepared for IHC score measurement of CD8 protein, and CD8-positive T cells were detected in the tumor tissues of each treated group using an anti-mouse CD8α antibody (clone KT15) (Gene-Tex).

==Tumor Volume==

On days 1, 3, 8, 11, 15, 18, and 22 after initiation of administration, the tumor volume was measured using calipers.

The proportion of CD8-positive T cells relative to all viable cells, compared with the control group, was not significantly different in the anti-PD-L1 antibody single administration group and the anti-VEGF antibody single administration group, but was significantly higher in the group with combined use of both antibodies (combined use) (FIG. 3A). The proportion of granzyme B-positive CD8-positive T cells relative to all viable cells, compared with the control group, was also not significantly different in the anti-PD-L1 antibody single administration group and the anti-VEGF antibody single administration group, but was significantly higher in the group with combined use of both antibodies (combined use) (FIG. 3B).

The IHC score for CD8 protein (graph made by setting as follow: no findings (−), very slight (±), slight (+), moderate (++), marked (+++), then converting into scores ("−"=0, "±"=1, "+"=2, "++"=3, "+++"=4)) on day 8 after initiation of administration was significantly higher in mice that received the combined use of 6E11 and B20-4.1.1 compared with the control group and the anti-VEGF antibody single administration group (FIG. 3C, D).

The results above demonstrated that the single administration of the anti-PD-L1 antibody 6E11 did not affect the number of intratumoral CD8-positive T cells. Additionally, granzyme B-positive CD8-positive T cells represent activated CD8-positive T cells.

As such, it was shown that even for cancer in which the single administration of an anti-PD-L1 antibody, which is a PD-1/PD-L1 signaling inhibitor, has no influence on intratumoral activated CD8-positive T cells, the combined use of an anti-PD-L1 antibody and an anti-VEGF antibody has the effect of significantly increasing the activated CD8-positive T cells that infiltrated into tumors compared with the control group and the anti-VEGF antibody single administration group.

With respect to the tumor volume, a significant difference was not observed in the tumor volume with or without the administration of the anti-CD8α antibody in the control group and the anti-VEGF antibody single administration group. Meanwhile, the administration of the anti-CD8α antibody in the combined use group (combined use) (combined use+anti-CD8α antibody) significantly increased the tumor volume to the same level as the anti-VEGF antibody single administration group (FIG. 4A).

FIG. 4B shows a comparison of tumor volumes on day 22 after initiation of administration for each group. In the group with combined use of the anti-PD-L1 antibody and the anti-VEGF antibody ("+" for both the anti-PD-L1 antibody and the anti-VEGF antibody), the tumor volume was significantly reduced, i.e., a significantly higher anti-tumor effect was obtained, compared with the control group (all "−") or the anti-VEGF antibody single administration group ("+" for only the anti-VEGF antibody). In the group with combined use of the anti-CD8α antibody in addition to the combined use of the anti-PD-L1 antibody and the anti-VEGF antibody (all "+"), the tumor volume increased to the same level as the anti-VEGF antibody single administration group. That is, the increase in the anti-tumor effect induced by the combined use was canceled.

The results above demonstrated that intratumoral CD8-positive T cells mediated the increase in the anti-tumor effect induced by the combined use of the anti-PD-L1 antibody and the anti-VEGF antibody.

Example 3

Effect on intratumoral CXCL9 protein expression and contribution to the increase in intratumoral CD8-positive T cells of the combined use of an anti-PD-L1 antibody and an anti-VEGF antibody in OV2944-HM-1 cancer bearing mice ==Treatment Method==

The day of randomization was the day on which administration of the agents began, 5 mg/kg of 6E11 antibody was intraperitoneally administered to the OV2944-HM-1 cancer bearing mice twice a week, and 10 mg/kg of B20-4.1.1 was intraperitoneally administered to the OV2944-HM-1 cancer bearing mice once a week. An anti-mouse CXCR3 antibody (clone CXCR3-173) was intraperitoneally administered to the OV2944-HM-1 cancer bearing mice at 100 µg/mouse twice a week. Mouse IgG was administered at the same dose as the control for each antibody.

==CXCL9 Protein Expression==

On day 8 after initiation of administration, tumors were extracted from the mice, and the CXCL9 protein expression level in the tumor tissues was quantified by ELISA using Quantikine ELISA (Mouse CSCL9/MIG) (R&D Systems).

With respect to the CXCL9 protein expression level, a significant difference was not observed in the anti-PD-L1 antibody single administration group and the anti-VEGF antibody single administration group compared with the control group. In the group with combined use of the anti-PD-L1 antibody and the anti-VEGF antibody (combined use), the CXCL9 protein expression level was significantly higher compared with the control group or the anti-VEGF antibody single administration group (FIG. 5A).

Moreover, in the group administered with the anti-CXCR3 antibody in addition to the anti-PD-L1 antibody and the anti-VEGF antibody (all "+"), the proportion of CD8-positive T cells in all viable cells, compared with the group with combined use of the anti-PD-L1 antibody and the anti-VEGF antibody, was significantly lower and was at the same level as the control group (FIG. 5B). This indicates that the anti-CXCR3 antibody-induced blockage of the CXCR3 axis in CD8-positive T cells canceled the increase in the anti-tumor effect observed with the combined use of the anti-PD-L1 antibody and the anti-VEGF antibody.

It was shown in Example 2 that the increase in intratumoral CD8-positive T cells, observed in the group with combined used of the anti-PD-L1 antibody and the anti-VEGF antibody, contributed to the increase in the anti-tumor effect.

CXCL9 is a T cell chemotactic factor that acts through binding to CXCR3, a receptor expressed on T cells, and the present example (FIG. 5) demonstrated that the higher intratumoral CXCL9 protein concentration, observed in the group with combined use of the anti-PD-L1 antibody and the anti-VEGF antibody, contributed to the enhanced infiltration into tumors via the CXCR3 axis in CD8-positive T cells. Taking Example 2 and Example 3 together, the strong enhancement in the anti-tumor effect by the combined use of the anti-PD-L1 antibody and the anti-VEGF antibody shown in FIG. 2 and FIG. 4 is believed to be caused by an increase in intratumoral CD8-positive T cells induced by an increase in intratumoral CXCL9 protein concentration.

Example 4

Effect on MHC Class I molecules on tumor cells of the combined use of an anti-PD-L1 antibody and an anti-VEGF antibody in OV2944-HM-1 cancer bearing mice
==Treatment Method==
The day of randomization was the day on which administration of the agents began, 5 mg/kg of 6E11 antibody was intraperitoneally administered to the OV2944-HM-1 cancer bearing mice twice a week, and 10 mg/kg of B20-4.1.1 was intraperitoneally administered to the OV2944-HM-1 cancer bearing mice once a week. Mouse IgG was administered at the same dose as the control for each antibody.
==MHC Class I Molecules==
On day 8 after initiation of administration, tumors were extracted from the mice, and cells dispersed with gentleMACS (Registered Trademark) Octo Dissociator were quantified for the protein expression level of MHC class I molecules on tumor cells by flow cytometry using an anti-mouse H-2Kk (C3H) antibody-FITC (BioLegend).

Compared with the other administration groups, MHC class I molecule protein expression was significantly increased in the group with combined use of the anti-PD-L1 antibody and the anti-VEGF antibody (FIG. 6).

MHC class I molecules present antigens to CD8-positive T cells and play an important role in the removal of cancer cells, etc. From the present results, the combined use of the anti-PD-L1 antibody and the anti-VEGF antibody is believed to enhance presentation of tumor-specific antigens to CD8-positive T cells.

Example 5

Effect on intratumoral microvessel density of the combined use of an anti-PD-L1 antibody and an anti-VEGF antibody in OV2944-HM-1 cancer bearing mice
==Treatment Method==
The day of randomization was the day on which administration of the agents began, 5 mg/kg of 6E11 antibody was intraperitoneally administered to the OV2944-HM-1 cancer bearing mice twice a week, and 10 mg/kg of B20-4.1.1 was intraperitoneally administered to the OV2944-HM-1 cancer bearing mice once a week. Mouse IgG was administered at the same dose as the control for each antibody.
==Intratumoral Microvessel Density==
Intratumoral microvessel density (MVD) was measured for tumors extracted from the mice on day 8 after initiation of administration. CD31 protein was detected in the tumor tissues by immunohistochemistry using a rat anti-mouse CD31 monoclonal antibody (clone MEC 13.3) (Becton Dickinson and Company) and Rat HRP-Polymer, 1-Step (Mouse adsorbed) (Biocare Medical), and MVD was calculated from the ratio of CD31-positive areas relative to the total observation area (3-6 live tissue fields per section). With respect to MVD, the microvessel density was not significantly different in the anti-PD-L1 antibody single administration group compared with the control group. Meanwhile, the microvessel density was significantly lower in the group with combined use of the anti-PD-L1 antibody and the anti-VEGF antibody (combined use) and the anti-VEGF antibody single administration group, compared with the control group or the anti-PD-L1 antibody single administration group (FIG. 7).

Intratumoral microvessel density is involved in cancer progression. From the present results, it is believed that even for cancer resistant to an anti-PD-L1 antibody, which is a PD-1/PD-L1 signaling inhibitor, the combined use of an anti-PD-L1 antibody and an anti-VEGF antibody and the administration of an anti-VEGF antibody have the effect of significantly reducing intratumoral microvessel density, i.e., an anti-tumor effect.

Based on the present example and Examples 1-4, the combined use of an anti-PD-L1 antibody, which is a PD-1/PD-L1 signaling inhibitor, and an anti-VEGF antibody, which is a VEGF signaling inhibitor, was shown to provide strong anti-tumor effects through an increase in intratumoral CXCL9 and the subsequent enhancement in CD8-positive T cell infiltration into tumors in a PD-L1 signaling inhibitor-unresponsive mouse model having PD-L1$^{low}$ tumors and an immune desert-like phenotype.

INDUSTRIAL APPLICABILITY

The present invention is useful for cancer treatment.

The invention claimed is:

1. A method of treating cancer resistant to a PD-1/PD-L1 signaling inhibitor in an individual, wherein the method comprises examining the individual for the presence or absence of resistance to a PD-1/PD-L1 signaling inhibitor, selecting the individual for treatment based upon the determination that the individual has cancer resistant to a PD-1/PD-L1 signaling inhibitor, and administering bevacizumab and MPDL3280A to the individual.

2. The method of claim 1, wherein the MPDL3280A and the bevacizumab are administered in combination.

3. The method of claim 1, wherein the MPDL3280A and the bevacizumab are administered concurrently, separately, or sequentially.

4. The method of claim 3, wherein the MPDL3280A and the bevacizumab are administered sequentially.

5. The method of claim 3, wherein the MPDL3280A and the bevacizumab are administered separately.

6. The method of claim 1, wherein the cancer is ovarian cancer or colon cancer.

7. The method of claim 1, wherein the PD-1/PD-L1 signaling inhibitor is MPDL3280A.

8. The method of claim 1, wherein the cancer is ovarian cancer.

* * * * *

SEQUENCE LISTING

<160> NUMBER OF SEQ ID NOS: 63

<210> SEQ ID NO 1
<211> LENGTH: 448
<212> TYPE: PRT
<213> ORGANISM: Artificial Sequence
<220> FEATURE:

-continued

<223> OTHER INFORMATION: Atezolizumab HC

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

-continued

```
Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 2
<211> LENGTH: 214
<212> TYPE: PRT
<213> ORGANISM: Artificial Sequence
<220> FEATURE:
<223> OTHER INFORMATION: Atezolizumab LC

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 118
<212> TYPE: PRT
<213> ORGANISM: Artificial Sequence
<220> FEATURE:
<223> OTHER INFORMATION: Atezolizumab VH

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45
```

```
Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
                100                 105                 110

Leu Val Thr Val Ser Ser
        115
```

<210> SEQ ID NO 4
<211> LENGTH: 107
<212> TYPE: PRT
<213> ORGANISM: Artificial Sequence
<220> FEATURE:
<223> OTHER INFORMATION: Atezolizumab VL

<400> SEQUENCE: 4

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105
```

<210> SEQ ID NO 5
<211> LENGTH: 10
<212> TYPE: PRT
<213> ORGANISM: Artificial Sequence
<220> FEATURE:
<223> OTHER INFORMATION: Atezolizumab HCDR1

<400> SEQUENCE: 5

```
Gly Phe Thr Phe Ser Asp Ser Trp Ile His
1               5                   10
```

<210> SEQ ID NO 6
<211> LENGTH: 18
<212> TYPE: PRT
<213> ORGANISM: Artificial Sequence
<220> FEATURE:
<223> OTHER INFORMATION: Atezolizumab HCDR2

<400> SEQUENCE: 6

```
Ala Trp Ile Ser Pro Tyr Gly Gly Ser Thr Tyr Tyr Ala Asp Ser Val
1               5                   10                  15

Lys Gly
```

<210> SEQ ID NO 7
<211> LENGTH: 9
<212> TYPE: PRT

-continued

```
<213> ORGANISM: Artificial Sequence
<220> FEATURE:
<223> OTHER INFORMATION: Atezolizumab HCDR3

<400> SEQUENCE: 7

Arg His Trp Pro Gly Gly Phe Asp Tyr
1               5

<210> SEQ ID NO 8
<211> LENGTH: 11
<212> TYPE: PRT
<213> ORGANISM: Artificial Sequence
<220> FEATURE:
<223> OTHER INFORMATION: Atezolizumab LCDR1

<400> SEQUENCE: 8

Arg Ala Ser Gln Asp Val Ser Thr Ala Val Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Atezolizumab LCDR2

<400> SEQUENCE: 9

Ser Ala Ser Phe Leu Tyr Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Atezolizumab LCDR3

<400> SEQUENCE: 10

Gln Gln Tyr Leu Tyr His Pro Ala Thr
1               5

<210> SEQ ID NO 11
<211> LENGTH: 450
<212> TYPE: PRT
<213> ORGANISM: Artificial Sequence
<220> FEATURE:
<223> OTHER INFORMATION: Avelumab HC

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110
```

-continued

```
Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
    450
```

```
<210> SEQ ID NO 12
<211> LENGTH: 216
<212> TYPE: PRT
<213> ORGANISM: Artificial Sequence
<220> FEATURE:
<223> OTHER INFORMATION: Avelumab LC

<400> SEQUENCE: 12

Gln Ser Ala Leu Thr Gln Pro Ala Ser Val Ser Gly Ser Pro Gly Gln
1               5                   10                  15
```

```
Ser Ile Thr Ile Ser Cys Thr Gly Thr Ser Ser Asp Val Gly Gly Tyr
            20              25              30

Asn Tyr Val Ser Trp Tyr Gln Gln His Pro Gly Lys Ala Pro Lys Leu
        35              40              45

Met Ile Tyr Asp Val Ser Asn Arg Pro Ser Gly Val Ser Asn Arg Phe
    50              55              60

Ser Gly Ser Lys Ser Gly Asn Thr Ala Ser Leu Thr Ile Ser Gly Leu
65              70              75              80

Gln Ala Glu Asp Glu Ala Asp Tyr Tyr Cys Ser Ser Tyr Thr Ser Ser
                85              90              95

Ser Thr Arg Val Phe Gly Thr Gly Thr Lys Val Thr Val Leu Gly Gln
            100             105             110

Pro Lys Ala Asn Pro Thr Val Thr Leu Phe Pro Pro Ser Ser Glu Glu
        115             120             125

Leu Gln Ala Asn Lys Ala Thr Leu Val Cys Leu Ile Ser Asp Phe Tyr
    130             135             140

Pro Gly Ala Val Thr Val Ala Trp Lys Ala Asp Gly Ser Pro Val Lys
145             150             155             160

Ala Gly Val Glu Thr Thr Lys Pro Ser Lys Gln Ser Asn Asn Lys Tyr
                165             170             175

Ala Ala Ser Ser Tyr Leu Ser Leu Thr Pro Glu Gln Trp Lys Ser His
            180             185             190

Arg Ser Tyr Ser Cys Gln Val Thr His Glu Gly Ser Thr Val Glu Lys
        195             200             205

Thr Val Ala Pro Thr Glu Cys Ser
    210             215
```

```
<210> SEQ ID NO 13
<211> LENGTH: 120
<212> TYPE: PRT
<213> ORGANISM: Artificial Sequence
<220> FEATURE:
<223> OTHER INFORMATION: Avelumab VH

<400> SEQUENCE: 13
```

```
Glu Val Gln Leu Leu Glu Ser Gly Gly Gly Leu Val Gln Pro Gly Gly
1               5               10              15

Ser Leu Arg Leu Ser Cys Ala Ala Ser Gly Phe Thr Phe Ser Ser Tyr
            20              25              30

Ile Met Met Trp Val Arg Gln Ala Pro Gly Lys Gly Leu Glu Trp Val
        35              40              45

Ser Ser Ile Tyr Pro Ser Gly Gly Ile Thr Phe Tyr Ala Asp Thr Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Ile Lys Leu Gly Thr Val Thr Thr Val Asp Tyr Trp Gly Gln
            100             105             110

Gly Thr Leu Val Thr Val Ser Ser
        115             120
```

```
<210> SEQ ID NO 14
<211> LENGTH: 110
<212> TYPE: PRT
<213> ORGANISM: Artificial Sequence
<220> FEATURE:
```

<223> OTHER INFORMATION: Avelumab VL

<400> SEQUENCE: 14

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110
```

<210> SEQ ID NO 15
<211> LENGTH: 5
<212> TYPE: PRT
<213> ORGANISM: Artificial Sequence
<220> FEATURE:
<223> OTHER INFORMATION: Avelumab HCDR1

<400> SEQUENCE: 15

```
Ser Tyr Ile Met Met
1               5
```

<210> SEQ ID NO 16
<211> LENGTH: 17
<212> TYPE: PRT
<213> ORGANISM: Artificial Sequence
<220> FEATURE:
<223> OTHER INFORMATION: Avelumab HCDR2

<400> SEQUENCE: 16

```
Ser Ile Tyr Pro Ser Gly Gly Ile Thr Phe Tyr Ala Asp Thr Val Lys
1               5                   10                  15

Gly
```

<210> SEQ ID NO 17
<211> LENGTH: 11
<212> TYPE: PRT
<213> ORGANISM: Artificial Sequence
<220> FEATURE:
<223> OTHER INFORMATION: Avelumab HCDR3

<400> SEQUENCE: 17

```
Ile Lys Leu Gly Thr Val Thr Thr Val Asp Tyr
1               5                   10
```

<210> SEQ ID NO 18
<211> LENGTH: 14
<212> TYPE: PRT
<213> ORGANISM: Artificial Sequence
<220> FEATURE:
<223> OTHER INFORMATION: Avelumab LCDR1

<400> SEQUENCE: 18

```
Thr Gly Thr Ser Ser Asp Val Gly Gly Tyr Asn Tyr Val Ser
1               5                   10
```

-continued

<210> SEQ ID NO 19
<211> LENGTH: 7
<212> TYPE: PRT
<213> ORGANISM: Artificial Sequence
<220> FEATURE:
<223> OTHER INFORMATION: Avelumab LCDR2

<400> SEQUENCE: 19

Asp Val Ser Asn Arg Pro Ser
1               5

<210> SEQ ID NO 20
<211> LENGTH: 10
<212> TYPE: PRT
<213> ORGANISM: Artificial Sequence
<220> FEATURE:
<223> OTHER INFORMATION: Avelumab LCDR3

<400> SEQUENCE: 20

Ser Ser Tyr Thr Ser Ser Ser Thr Arg Val
1               5                   10

<210> SEQ ID NO 21
<211> LENGTH: 451
<212> TYPE: PRT
<213> ORGANISM: Artificial Sequence
<220> FEATURE:
<223> OTHER INFORMATION: Durvalumab HC

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly

```
225                 230                 235                 240
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
    450

<210> SEQ ID NO 22
<211> LENGTH: 215
<212> TYPE: PRT
<213> ORGANISM: Artificial Sequence
<220> FEATURE:
<223> OTHER INFORMATION: Durvalumab LC

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
                20                  25                  30

Tyr Leu Ala Trp Tyr Gln Gln Lys Pro Gly Gln Ala Pro Arg Leu Leu
            35                  40                  45

Ile Tyr Asp Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
```

```
        130                135                140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 23
<211> LENGTH: 121
<212> TYPE: PRT
<213> ORGANISM: Artificial Sequence
<220> FEATURE:
<223> OTHER INFORMATION: Durvalumab VH

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
                20                  25                  30

Trp Met Ser Trp Val Arg Gln Ala Pro Gly Lys Gly Leu Glu Trp Val
                35                  40                  45

Ala Asn Ile Lys Gln Asp Gly Ser Glu Lys Tyr Tyr Val Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
                100                 105                 110

Gln Gly Thr Leu Val Thr Val Ser Ser
            115                 120

<210> SEQ ID NO 24
<211> LENGTH: 108
<212> TYPE: PRT
<213> ORGANISM: Artificial Sequence
<220> FEATURE:
<223> OTHER INFORMATION: Durvalumab VL

<400> SEQUENCE: 24

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
                20                  25                  30

Tyr Leu Ala Trp Tyr Gln Gln Lys Pro Gly Gln Ala Pro Arg Leu Leu
                35                  40                  45

Ile Tyr Asp Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95
```

-continued

```
Trp Thr Phe Gly Gln Gly Thr Lys Val Glu Ile Lys
            100                 105

<210> SEQ ID NO 25
<211> LENGTH: 360
<212> TYPE: PRT
<213> ORGANISM: Artificial Sequence
<220> FEATURE:
<223> OTHER INFORMATION: KN035 HC

<400> SEQUENCE: 25

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Glu Pro Lys Ser Ser Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Ala Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Gly Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350
```

Ser Leu Ser Leu Ser Pro Gly Lys
        355                 360

<210> SEQ ID NO 26
<211> LENGTH: 112
<212> TYPE: PRT
<213> ORGANISM: Artificial Sequence
<220> FEATURE:
<223> OTHER INFORMATION: KN035 VH

<400> SEQUENCE: 26

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

<210> SEQ ID NO 27
<211> LENGTH: 10
<212> TYPE: PRT
<213> ORGANISM: Artificial Sequence
<220> FEATURE:
<223> OTHER INFORMATION: KN035 HCDR1

<400> SEQUENCE: 27

Gly Lys Met Ser Ser Arg Arg Cys Met Ala
1               5                   10

<210> SEQ ID NO 28
<211> LENGTH: 17
<212> TYPE: PRT
<213> ORGANISM: Artificial Sequence
<220> FEATURE:
<223> OTHER INFORMATION: KN035 HCDR2

<400> SEQUENCE: 28

Lys Leu Leu Thr Thr Ser Gly Ser Thr Tyr Leu Ala Asp Ser Val Lys
1               5                   10                  15

Gly

<210> SEQ ID NO 29
<211> LENGTH: 19
<212> TYPE: PRT
<213> ORGANISM: Artificial Sequence
<220> FEATURE:
<223> OTHER INFORMATION: KN035 HCDR3

<400> SEQUENCE: 29

Asp Ser Phe Glu Asp Pro Thr Cys Thr Leu Val Thr Ser Ser Gly Ala
1               5                   10                  15

Phe Gln Tyr

<210> SEQ ID NO 30

```
<211> LENGTH: 442
<212> TYPE: PRT
<213> ORGANISM: Artificial Sequence
<220> FEATURE:
<223> OTHER INFORMATION: CX-072 HC

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ser Ile Trp Arg Asn Gly Ile Val Thr Val Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ser Ala Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Pro
        210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
        370                 375                 380
```

Asn Asn Tyr Lys Thr Thr Pro Pro Val Leu Asp Ser Asp Gly Ser Phe
385                 390             395                 400

Phe Leu Tyr Ser Arg Leu Thr Val Asp Lys Ser Arg Trp Gln Glu Gly
                405             410             415

Asn Val Phe Ser Cys Ser Val Met His Glu Ala Leu His Asn His Tyr
                420             425             430

Thr Gln Lys Ser Leu Ser Leu Ser Leu Gly
        435             440

<210> SEQ ID NO 31
<211> LENGTH: 264
<212> TYPE: PRT
<213> ORGANISM: Artificial Sequence
<220> FEATURE:
<223> OTHER INFORMATION: CX-072 LC

<400> SEQUENCE: 31

Gln Gly Gln Ser Gly Ser Gly Ile Ala Leu Cys Pro Ser His Phe Cys
1               5               10              15

Gln Leu Pro Gln Thr Gly Gly Gly Ser Ser Gly Gly Ser Gly Gly Ser
            20              25              30

Gly Gly Ile Ser Ser Gly Leu Leu Ser Gly Arg Ser Asp Asn His Gly
        35              40              45

Gly Ser Asp Ile Gln Met Thr Gln Ser Pro Ser Ser Leu Ser Ala Ser
    50              55              60

Val Gly Asp Arg Val Thr Ile Thr Cys Arg Ala Ser Gln Ser Ile Ser
65              70              75              80

Ser Tyr Leu Asn Trp Tyr Gln Gln Lys Pro Gly Lys Ala Pro Lys Leu
                85              90              95

Leu Ile Tyr Ala Ala Ser Ser Leu Gln Ser Gly Val Pro Ser Arg Phe
            100             105             110

Ser Gly Ser Gly Ser Gly Thr Asp Phe Thr Leu Thr Ile Ser Ser Leu
        115             120             125

Gln Pro Glu Asp Phe Ala Thr Tyr Tyr Cys Gln Gln Asp Asn Gly Tyr
    130             135             140

Pro Ser Thr Phe Gly Gly Gly Thr Lys Val Glu Ile Lys Arg Thr Val
145             150             155             160

Ala Ala Pro Ser Val Phe Ile Phe Pro Pro Ser Asp Glu Gln Leu Lys
            165             170             175

Ser Gly Thr Ala Ser Val Val Cys Leu Leu Asn Asn Phe Tyr Pro Arg
        180             185             190

Glu Ala Lys Val Gln Trp Lys Val Asp Asn Ala Leu Gln Ser Gly Asn
    195             200             205

Ser Gln Glu Ser Val Thr Glu Gln Asp Ser Lys Asp Ser Thr Tyr Ser
    210             215             220

Leu Ser Ser Thr Leu Thr Leu Ser Lys Ala Asp Tyr Glu Lys His Lys
225             230             235             240

Val Tyr Ala Cys Glu Val Thr His Gln Gly Leu Ser Ser Pro Val Thr
                245             250             255

Lys Ser Phe Asn Arg Gly Glu Cys
        260

<210> SEQ ID NO 32
<211> LENGTH: 116
<212> TYPE: PRT
<213> ORGANISM: Artificial Sequence

```
<220> FEATURE:
<223> OTHER INFORMATION: CX-072 VH

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ser Ile Trp Arg Asn Gly Ile Val Thr Val Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ser Ala Ala Phe Asp Tyr Trp Gly Gln Gly Thr Leu Val
                100                 105                 110

Thr Val Ser Ser
        115

<210> SEQ ID NO 33
<211> LENGTH: 107
<212> TYPE: PRT
<213> ORGANISM: Artificial Sequence
<220> FEATURE:
<223> OTHER INFORMATION: CX-072 VL

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Asn Gly Tyr Pro Ser
                85                  90                  95

Thr Phe Gly Gly Gly Thr Lys Val Glu Ile Lys
            100                 105

<210> SEQ ID NO 34
<211> LENGTH: 453
<212> TYPE: PRT
<213> ORGANISM: Artificial Sequence
<220> FEATURE:
<223> OTHER INFORMATION: LY3300054 HC

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45
```

```
Gly Gly Ile Ile Pro Ile Phe Gly Thr Ala Asn Tyr Ala Gln Lys Phe
    50              55                  60

Gln Gly Arg Val Thr Ile Thr Ala Asp Lys Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Ser Pro Asp Tyr Ser Pro Tyr Tyr Tyr Gly Met Asp Val
            100             105             110

Trp Gly Gln Gly Thr Thr Val Thr Val Ser Ser Ala Ser Thr Lys Gly
            115             120             125

Pro Ser Val Phe Pro Leu Ala Pro Ser Ser Lys Ser Thr Ser Gly Gly
    130             135             140

Thr Ala Ala Leu Gly Cys Leu Val Lys Asp Tyr Phe Pro Glu Pro Val
145             150             155             160

Thr Val Ser Trp Asn Ser Gly Ala Leu Thr Ser Gly Val His Thr Phe
                165             170             175

Pro Ala Val Leu Gln Ser Ser Gly Leu Tyr Ser Leu Ser Ser Val Val
            180             185             190

Thr Val Pro Ser Ser Ser Leu Gly Thr Gln Thr Tyr Ile Cys Asn Val
            195             200             205

Asn His Lys Pro Ser Asn Thr Lys Val Asp Lys Arg Val Glu Pro Lys
    210             215             220

Ser Cys Asp Lys Thr His Thr Cys Pro Pro Cys Pro Ala Pro Glu Ala
225             230             235             240

Glu Gly Ala Pro Ser Val Phe Leu Phe Pro Pro Lys Pro Lys Asp Thr
            245             250             255

Leu Met Ile Ser Arg Thr Pro Glu Val Thr Cys Val Val Val Asp Val
            260             265             270

Ser His Glu Asp Pro Glu Val Lys Phe Asn Trp Tyr Val Asp Gly Val
            275             280             285

Glu Val His Asn Ala Lys Thr Lys Pro Arg Glu Glu Gln Tyr Asn Ser
    290             295             300

Thr Tyr Arg Val Val Ser Val Leu Thr Val Leu His Gln Asp Trp Leu
305             310             315             320

Asn Gly Lys Glu Tyr Lys Cys Lys Val Ser Asn Lys Ala Leu Pro Ser
            325             330             335

Ser Ile Glu Lys Thr Ile Ser Lys Ala Lys Gly Gln Pro Arg Glu Pro
            340             345             350

Gln Val Tyr Thr Leu Pro Pro Ser Arg Glu Glu Met Thr Lys Asn Gln
            355             360             365

Val Ser Leu Thr Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu His Asn His Tyr Thr Gln Lys Ser Leu Ser
            435             440             445

Leu Ser Pro Gly Lys
    450
```

<210> SEQ ID NO 35
<211> LENGTH: 216
<212> TYPE: PRT
<213> ORGANISM: Artificial Sequence
<220> FEATURE:
<223> OTHER INFORMATION: LY3300054 LC

<400> SEQUENCE: 35

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Gly Asn Ser Asn Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Ile Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215
```

<210> SEQ ID NO 36
<211> LENGTH: 123
<212> TYPE: PRT
<213> ORGANISM: Artificial Sequence
<220> FEATURE:
<223> OTHER INFORMATION: LY3300054 VH

<400> SEQUENCE: 36

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Ser Pro Asp Tyr Ser Pro Tyr Tyr Tyr Gly Met Asp Val
                100                    105                    110

Trp Gly Gln Gly Thr Thr Val Thr Val Ser Ser
        115                    120

<210> SEQ ID NO 37
<211> LENGTH: 110
<212> TYPE: PRT
<213> ORGANISM: Artificial Sequence
<220> FEATURE:
<223> OTHER INFORMATION: LY3300054 VL

<400> SEQUENCE: 37

Gln Ser Val Leu Thr Gln Pro Pro Ser Ala Ser Gly Thr Pro Gly Gln
1                    5                    10                    15

Arg Val Thr Ile Ser Cys Ser Gly Ser Ser Ser Asn Ile Gly Ser Asn
                20                    25                    30

Thr Val Asn Trp Tyr Gln Gln Leu Pro Gly Thr Ala Pro Lys Leu Leu
            35                    40                    45

Ile Tyr Gly Asn Ser Asn Arg Pro Ser Gly Val Pro Asp Arg Phe Ser
    50                    55                    60

Gly Ser Lys Ser Gly Thr Ser Ala Ser Leu Ala Ile Ser Gly Leu Gln
65                    70                    75                    80

Ser Glu Asp Glu Ala Asp Tyr Tyr Cys Gln Ser Tyr Asp Ser Ser Leu
                85                    90                    95

Ser Gly Ser Val Phe Gly Gly Gly Ile Lys Leu Thr Val Leu
            100                    105                    110

<210> SEQ ID NO 38
<211> LENGTH: 13
<212> TYPE: PRT
<213> ORGANISM: Artificial Sequence
<220> FEATURE:
<223> OTHER INFORMATION: LY3300054 HCDR1

<400> SEQUENCE: 38

Lys Ala Ser Gly Gly Thr Phe Ser Ser Tyr Ala Ile Ser
1                    5                    10

<210> SEQ ID NO 39
<211> LENGTH: 17
<212> TYPE: PRT
<213> ORGANISM: Artificial Sequence
<220> FEATURE:
<223> OTHER INFORMATION: LY3300054 HCDR2

<400> SEQUENCE: 39

Gly Ile Ile Pro Ile Phe Gly Thr Ala Asn Tyr Ala Gln Lys Phe Gln
1                    5                    10                    15

Gly

<210> SEQ ID NO 40
<211> LENGTH: 16
<212> TYPE: PRT
<213> ORGANISM: Artificial Sequence
<220> FEATURE:
<223> OTHER INFORMATION: LY3300054 HCDR3

<400> SEQUENCE: 40

Ala Arg Ser Pro Asp Tyr Ser Pro Tyr Tyr Tyr Gly Met Asp Val
1                    5                    10                    15

```
<210> SEQ ID NO 41
<211> LENGTH: 13
<212> TYPE: PRT
<213> ORGANISM: Artificial Sequence
<220> FEATURE:
<223> OTHER INFORMATION: LY3300054 LCDR1

<400> SEQUENCE: 41

Ser Gly Ser Ser Ser Asn Ile Gly Ser Asn Thr Val Asn
1               5                   10

<210> SEQ ID NO 42
<211> LENGTH: 8
<212> TYPE: PRT
<213> ORGANISM: Artificial Sequence
<220> FEATURE:
<223> OTHER INFORMATION: LY3300054 LCDR2

<400> SEQUENCE: 42

Tyr Gly Asn Ser Asn Arg Pro Ser
1               5

<210> SEQ ID NO 43
<211> LENGTH: 11
<212> TYPE: PRT
<213> ORGANISM: Artificial Sequence
<220> FEATURE:
<223> OTHER INFORMATION: LY3300054 LCDR3

<400> SEQUENCE: 43

Gln Ser Tyr Asp Ser Ser Leu Ser Gly Ser Val
1               5                   10

<210> SEQ ID NO 44
<211> LENGTH: 453
<212> TYPE: PRT
<213> ORGANISM: Artificial Sequence
<220> FEATURE:
<223> OTHER INFORMATION: Bevacizumab HC

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
```

-continued

```
                    165                 170                 175
Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
        435                 440                 445

Leu Ser Pro Gly Lys
    450
```

```
<210> SEQ ID NO 45
<211> LENGTH: 214
<212> TYPE: PRT
<213> ORGANISM: Artificial Sequence
<220> FEATURE:
<223> OTHER INFORMATION: Bevacizumab LC

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
```

-continued

```
65                    70                    75                    80

Glu Asp Phe Ala Thr Tyr Tyr Cys Gln Gln Tyr Ser Thr Val Pro Trp
                85                    90                    95

Thr Phe Gly Gln Gly Thr Lys Val Glu Ile Lys Arg Thr Val Ala Ala
            100                   105                   110

Pro Ser Val Phe Ile Phe Pro Pro Ser Asp Glu Gln Leu Lys Ser Gly
            115                   120                   125

Thr Ala Ser Val Val Cys Leu Leu Asn Asn Phe Tyr Pro Arg Glu Ala
        130                   135                   140

Lys Val Gln Trp Lys Val Asp Asn Ala Leu Gln Ser Gly Asn Ser Gln
145                   150                   155                   160

Glu Ser Val Thr Glu Gln Asp Ser Lys Asp Ser Thr Tyr Ser Leu Ser
                165                   170                   175

Ser Thr Leu Thr Leu Ser Lys Ala Asp Tyr Glu Lys His Lys Val Tyr
            180                   185                   190

Ala Cys Glu Val Thr His Gln Gly Leu Ser Ser Pro Val Thr Lys Ser
            195                   200                   205

Phe Asn Arg Gly Glu Cys
    210

<210> SEQ ID NO 46
<211> LENGTH: 123
<212> TYPE: PRT
<213> ORGANISM: Artificial Sequence
<220> FEATURE:
<223> OTHER INFORMATION: Bevacizumab VH

<400> SEQUENCE: 46

Glu Val Gln Leu Val Glu Ser Gly Gly Gly Leu Val Gln Pro Gly Gly
1               5                   10                    15

Ser Leu Arg Leu Ser Cys Ala Ala Ser Gly Tyr Thr Phe Thr Asn Tyr
            20                    25                    30

Gly Met Asn Trp Val Arg Gln Ala Pro Gly Lys Gly Leu Glu Trp Val
        35                    40                    45

Gly Trp Ile Asn Thr Tyr Thr Gly Glu Pro Thr Tyr Ala Ala Asp Phe
    50                    55                    60

Lys Arg Arg Phe Thr Phe Ser Leu Asp Thr Ser Lys Ser Thr Ala Tyr
65                    70                    75                    80

Leu Gln Met Asn Ser Leu Arg Ala Glu Asp Thr Ala Val Tyr Tyr Cys
                85                    90                    95

Ala Lys Tyr Pro His Tyr Tyr Gly Ser Ser His Trp Tyr Phe Asp Val
            100                   105                   110

Trp Gly Gln Gly Thr Leu Val Thr Val Ser Ser
        115                   120

<210> SEQ ID NO 47
<211> LENGTH: 107
<212> TYPE: PRT
<213> ORGANISM: Artificial Sequence
<220> FEATURE:
<223> OTHER INFORMATION: Bevacizumab VL

<400> SEQUENCE: 47

Asp Ile Gln Met Thr Gln Ser Pro Ser Ser Leu Ser Ala Ser Val Gly
1               5                   10                    15

Asp Arg Val Thr Ile Thr Cys Ser Ala Ser Gln Asp Ile Ser Asn Tyr
            20                    25                    30
```

```
Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105
```

```
<210> SEQ ID NO 48
<211> LENGTH: 10
<212> TYPE: PRT
<213> ORGANISM: Artificial Sequence
<220> FEATURE:
<223> OTHER INFORMATION: Bevacizumab HCDR1

<400> SEQUENCE: 48

Gly Tyr Thr Phe Thr Asn Tyr Gly Met Asn
1               5                   10
```

```
<210> SEQ ID NO 49
<211> LENGTH: 17
<212> TYPE: PRT
<213> ORGANISM: Artificial Sequence
<220> FEATURE:
<223> OTHER INFORMATION: Bevacizumab HCDR2

<400> SEQUENCE: 49

Trp Ile Asn Thr Tyr Thr Gly Glu Pro Thr Tyr Ala Ala Asp Phe Lys
1               5                   10                  15

Arg
```

```
<210> SEQ ID NO 50
<211> LENGTH: 14
<212> TYPE: PRT
<213> ORGANISM: Artificial Sequence
<220> FEATURE:
<223> OTHER INFORMATION: Bevacizumab HCDR3

<400> SEQUENCE: 50

Tyr Pro His Tyr Tyr Gly Ser Ser His Trp Tyr Phe Asp Val
1               5                   10
```

```
<210> SEQ ID NO 51
<211> LENGTH: 11
<212> TYPE: PRT
<213> ORGANISM: Artificial Sequence
<220> FEATURE:
<223> OTHER INFORMATION: Bevacizumab LCDR1

<400> SEQUENCE: 51

Ser Ala Ser Gln Asp Ile Ser Asn Tyr Leu Asn
1               5                   10
```

```
<210> SEQ ID NO 52
<211> LENGTH: 7
<212> TYPE: PRT
<213> ORGANISM: Artificial Sequence
<220> FEATURE:
<223> OTHER INFORMATION: Bevacizumab LCDR2

<400> SEQUENCE: 52
```

-continued

```
Phe Thr Ser Ser Leu His Ser
1               5

<210> SEQ ID NO 53
<211> LENGTH: 9
<212> TYPE: PRT
<213> ORGANISM: Artificial Sequence
<220> FEATURE:
<223> OTHER INFORMATION: Bevacizumab LCDR3

<400> SEQUENCE: 53

Gln Gln Tyr Ser Thr Val Pro Trp Thr
1               5

<210> SEQ ID NO 54
<211> LENGTH: 446
<212> TYPE: PRT
<213> ORGANISM: Artificial Sequence
<220> FEATURE:
<223> OTHER INFORMATION: Ramucirumab HC

<400> SEQUENCE: 54

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Met Val
            100                 105                 110

Thr Val Ser Ser Ala Ser Thr Lys Gly Pro Ser Val Leu Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285
```

-continued

```
Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 55
<211> LENGTH: 214
<212> TYPE: PRT
<213> ORGANISM: Artificial Sequence
<220> FEATURE:
<223> OTHER INFORMATION: Ramucirumab LC

<400> SEQUENCE: 55

Asp Ile Gln Met Thr Gln Ser Pro Ser Ser Val Ser Ala Ser Ile Gly
1               5                   10                  15

Asp Arg Val Thr Ile Thr Cys Arg Ala Ser Gln Gly Ile Asp Asn Trp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Asp Thr Gly Val Pro Ser Arg Phe Ser Gly
    50                  55                  60

Ser Gly Ser Gly Thr Tyr Phe Thr Leu Thr Ile Ser Ser Leu Gln Ala
65                  70                  75                  80

Glu Asp Phe Ala Val Tyr Phe Cys Gln Gln Ala Lys Ala Phe Pro Pro
                85                  90                  95

Thr Phe Gly Gly Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205
```

-continued

Phe Asn Arg Gly Glu Cys
    210

<210> SEQ ID NO 56
<211> LENGTH: 116
<212> TYPE: PRT
<213> ORGANISM: Artificial Sequence
<220> FEATURE:
<223> OTHER INFORMATION: Ramucirumab VH

<400> SEQUENCE: 56

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Met Val
            100                 105                 110

Thr Val Ser Ser
        115

<210> SEQ ID NO 57
<211> LENGTH: 107
<212> TYPE: PRT
<213> ORGANISM: Artificial Sequence
<220> FEATURE:
<223> OTHER INFORMATION: Ramucirumab VL

<400> SEQUENCE: 57

Asp Ile Gln Met Thr Gln Ser Pro Ser Ser Val Ser Ala Ser Ile Gly
1               5                   10                  15

Asp Arg Val Thr Ile Thr Cys Arg Ala Ser Gln Gly Ile Asp Asn Trp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Asp Thr Gly Val Pro Ser Arg Phe Ser Gly
    50                  55                  60

Ser Gly Ser Gly Thr Tyr Phe Thr Leu Thr Ile Ser Ser Leu Gln Ala
65                  70                  75                  80

Glu Asp Phe Ala Val Tyr Phe Cys Gln Gln Ala Lys Ala Phe Pro Pro
                85                  90                  95

Thr Phe Gly Gly Gly Thr Lys Val Asp Ile Lys
            100                 105

<210> SEQ ID NO 58
<211> LENGTH: 15
<212> TYPE: PRT
<213> ORGANISM: Artificial Sequence
<220> FEATURE:
<223> OTHER INFORMATION: Ramucirumab HCDR1

<400> SEQUENCE: 58

-continued

```
Ala Ala Ser Gly Phe Thr Phe Ser Ser Tyr Ser Met Asn Trp Val
1               5                   10                  15

<210> SEQ ID NO 59
<211> LENGTH: 17
<212> TYPE: PRT
<213> ORGANISM: Artificial Sequence
<220> FEATURE:
<223> OTHER INFORMATION: Ramucirumab HCDR2

<400> SEQUENCE: 59

Ser Ile Ser Ser Ser Ser Ser Tyr Ile Tyr Tyr Ala Asp Ser Val Lys
1               5                   10                  15

Gly

<210> SEQ ID NO 60
<211> LENGTH: 7
<212> TYPE: PRT
<213> ORGANISM: Artificial Sequence
<220> FEATURE:
<223> OTHER INFORMATION: Ramucirumab HCDR3

<400> SEQUENCE: 60

Val Thr Asp Ala Phe Asp Ile
1               5

<210> SEQ ID NO 61
<211> LENGTH: 12
<212> TYPE: PRT
<213> ORGANISM: Artificial Sequence
<220> FEATURE:
<223> OTHER INFORMATION: Ramucirumab LCDR1

<400> SEQUENCE: 61

Arg Ala Ser Gln Gly Ile Asp Asn Trp Leu Gly Trp
1               5                   10

<210> SEQ ID NO 62
<211> LENGTH: 7
<212> TYPE: PRT
<213> ORGANISM: Artificial Sequence
<220> FEATURE:
<223> OTHER INFORMATION: Ramucirumab LCDR2

<400> SEQUENCE: 62

Asp Ala Ser Asn Leu Asp Thr
1               5

<210> SEQ ID NO 63
<211> LENGTH: 9
<212> TYPE: PRT
<213> ORGANISM: Artificial Sequence
<220> FEATURE:
<223> OTHER INFORMATION: Ramucirumab LCDR3

<400> SEQUENCE: 63

Gln Gln Ala Lys Ala Phe Pro Pro Thr
1               5
```